US007892731B2

(12) United States Patent
Oliver et al.

(10) Patent No.: US 7,892,731 B2
(45) Date of Patent: Feb. 22, 2011

(54) SYSTEM AND METHOD FOR INHIBITING THE DECRYPTION OF A NUCLEIC ACID PROBE SEQUENCE USED FOR THE DETECTION OF A SPECIFIC NUCLEIC ACID

(75) Inventors: Kerry G. Oliver, Austin, TX (US); Christy Weiss, Georgetown, TX (US); Rebecca Godbout, Georgetown, TX (US)

(73) Assignee: Radix Biosolutions, Ltd., Georgetown, TX (US)

( * ) Notice: Subject to any disclaimer, the term of this patent is extended or adjusted under 35 U.S.C. 154(b) by 495 days.

(21) Appl. No.: 10/957,215

(22) Filed: Oct. 1, 2004

(65) Prior Publication Data

US 2006/0073487 A1 Apr. 6, 2006

(51) Int. Cl.

| | |
|---|---|
| ***C12Q 1/68*** | (2006.01) |
| ***C12P 19/34*** | (2006.01) |
| ***C07H 21/02*** | (2006.01) |
| ***C07H 21/04*** | (2006.01) |

(52) U.S. Cl. ...................... 435/6; 435/91.31; 536/23.1; 536/24.3; 536/24.33

(58) Field of Classification Search .................... 435/6, 435/91.1; 536/23.1, 24.3, 24.33

See application file for complete search history.

(56) References Cited

U.S. PATENT DOCUMENTS

| | | | | |
|---|---|---|---|---|
| 5,736,330 | A | 4/1998 | Fulton | 435/6 |
| 5,780,233 | A * | 7/1998 | Guo et al. | 435/6 |
| 5,981,180 | A | 11/1999 | Chandler et al. | 435/6 |
| 6,057,107 | A | 5/2000 | Fulton | 435/6 |
| 6,344,316 | B1 * | 2/2002 | Lockhart et al. | 506/9 |
| 2005/0064457 | A1 * | 3/2005 | Lee | 435/6 |

FOREIGN PATENT DOCUMENTS

| | | | |
|---|---|---|---|
| WO | WO 97/27317 | * | 7/1997 |
| WO | WO 99/36564 | * | 7/1999 |
| WO | WO 00/39345 | | 7/2000 |

OTHER PUBLICATIONS

Ranade et al, High throughput genotyping with single nucleotide polymorphisms; 2001, 11, 1262-1268.*

Lim et al, Multiplex polymerase chain reaction assay for simultaneous detection of *Candida albicans* and *Candida dubliniensis*. 2002, The Journal of Microbiology, 40, 146-150.*

Guo et al., "Direct flourescence analysis of genetic polymorphisms by hybridization with oligonucleotide arrays on glass supports," *Nucleic Acids Research*, 22(24):5456-5465, 1994.

Lipshutz et al., "Using oligonucleotide probe arrays to access genetic diversity," *Biotechniques*, 19(3):442-447, 1995.

Pickering et al., "Flow cytometric assay for genotyping cytochrome p450 2C9 and 2C19: comparison with a microelectronic DNA array," *Amer J. Pharmacogenomics*, 4(3):199-207, 2004.

* cited by examiner

*Primary Examiner*—Dave Nguyen
*Assistant Examiner*—Narayan K Bhat
(74) *Attorney, Agent, or Firm*—Fulbright & Jaworski LLP

(57) ABSTRACT

Sequence-specific nucleic acid hybridization assays are used for the detection of specific genetic sequences as indicators of genetic anomalies, mutations, and disease propensity. In addition, they are used for the detection of various biological agents and infectious pathogens. Because a complementary probe or nucleic acid sequence is required to detect a sequence of interest in a hybridization-based assay, nucleic acid sequencing techniques can rapidly determine the specific probe sequence being used for detection. This allows reverse engineered assays to be produced rapidly. In addition, it enables the circumvention of hybridization-based assays for biological agent or infectious pathogen detection by providing the information necessary to create or alter nucleic acid sequences to produce false positives or false negatives. The present invention provides methods and compositions for inhibiting the identification of specific detection sequences. More specifically, the invention provides masking sequences that mask the identity of specific detection sequences.

34 Claims, 10 Drawing Sheets

| attomoles of specific target | Fluorescence Intensity: # of Masking Molecules Coupled to Beads | | | |
| --- | --- | --- | --- | --- |
| | 0 | 1 | 2 | 3 |
| 10000 | 13159 | 10302 | 7481 | 8861 |
| 3160 | 10025 | 8312 | 6236 | 6559 |
| 1000 | 5219 | 4995 | 3802 | 4537 |
| 316 | 2242 | 2208 | 1795 | 2000 |
| 100 | 829 | 896 | 742 | 815 |
| 31.6 | 377 | 404 | 342 | 384 |
| 10 | 264 | 252 | 259 | 157 |
| 0 | 212 | 191 | 198 | 112 |

FIG. 2B

| attomoles of specific target | Fluorescence Intensity: # of Masking Molecules Coupled to Beads | | | |
|---|---|---|---|---|
| | 0 | 1 | 2 | 3 |
| 10000 | 24583 | 24564 | 24481 | 24831 |
| 3160 | 26127 | 24392 | 24305 | 24468 |
| 1000 | 24005 | 23797 | 23126 | 23144 |
| 316 | 16831 | 15034 | 12369 | 14626 |
| 100 | 6081 | 5810 | 4091 | 5719 |
| 31.6 | 1769 | 1715 | 1184 | 1627 |
| 10 | 497 | 444 | 353 | 535 |
| 0 | 19 | 20 | 23 | 19 |

FIG. 3B

Fluorescence Intensity

| | # of Masking Molecules Coupled to Beads | | | |
|---|---|---|---|---|
| | 0 | 1 | 2 | 3 |
| Background | 139 | 139 | 169 | 166 |
| Negative Sample | 183 | 148 | 196 | 187 |
| Positive Sample 1 | 1485 | 769 | 742 | 928 |
| Positive Sample 2 | 1463 | 691 | 605 | 846 |

FIG. 4B

Fluorescence Intensity

| | # of Masking Primer Sets | | | |
|---|---|---|---|---|
| | 0 | 1 | 2 | 3 |
| Background | 139 | 173 | 166 | 181 |
| Negative Sample | 183 | 194 | 184 | 187 |
| Positive Sample 1 | 1485 | 1496 | 1525 | 1404 |
| Positive Sample 2 | 1463 | 1234 | 1595 | 1487 |

FIG. 5B

SEQUENCE LISTING

<160> NUMBER OF SEQ ID NOS: 20

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1
acgacgacga cgc 13

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic Primer

<400> SEQUENCE: 2
gtagtagtag tag 13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic Primer

<400> SEQUENCE: 3
cgtcatcgct ata 13

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Synthetic Primer

<400> SEQUENCE: 4
tactgctatc gct 13

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic Primer -continued

<400> SEQUENCE: 5
acgacgacga cgctttattg 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 6
gtagtagtag tagacctccc 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 7
cgtcatcgct atacaggagt 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 8
tactgctatc gctggacgaa 20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 9
tcagacaatt tagatttg 18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 10
aagcgatgca cgcgcact 18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic Primer -continued

<400> SEQUENCE: 11
cgctttgtgc acttgcaa 18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 12
gttacgccag gtacaggc 18

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 13
atggtgtaaa tctgtaccag t 21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 14
ttggtagcag cggtagagtt g 21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 15
tctcctaggt acatctaatc c 21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 16
actccgcagc atccgcgtac t 21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 17

-continued

```
gaataactcg ggccgggtgc g                                              21


<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 18

caatactgct gatacttaca a                                              21


<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 19

cgcagcgctc tagaactgca a                                              21


<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 20

ggcagtatta tcagtaccgg c                                              21
```

SYSTEM AND METHOD FOR INHIBITING THE DECRYPTION OF A NUCLEIC ACID PROBE SEQUENCE USED FOR THE DETECTION OF A SPECIFIC NUCLEIC ACID

BACKGROUND OF THE INVENTION

1. Field of the Invention

The present invention relates generally to the field of molecular biology. More particularly, it concerns the detection of nucleic acids. In specific embodiments, the invention concerns methods and compositions for inhibiting the identification of a nucleic acid probe sequence used for the detection of a specific nucleic acid.

2. Description of Related Art

Nucleic acid sequences are made up of four distinct chemical bases: adenine, cytosine, guanine, and thymine (uracil in the case of RNA). Specific gene sequences consist of combinations of these four bases in a very specific order. Cellular DNA exists as a double-stranded heteroduplex in which adenine bases associate with thymine through hydrogen bonding and cytosine bases associate with guanine. Generally, nucleic acid diagnostic assays take advantage of these specific associations in multiple ways. For example, a detection oligonucleotide (probe) complementary to the specific DNA sequence being detected can be labeled with a variety of different detection molecules then the sample DNA can be immobilized and the presence or absence of the sequence of interest is determined by the binding and subsequent detection of the labeled probe. Alternatively, the probe can be immobilized onto a solid surface and used to capture the sample sequence of interest. Detection occurs through labeling of the sample DNA or the detection of the double-stranded sample/probe heteroduplex. In the case of real-time detection of a sequence the probe oligonucleotide is used during an amplification process of the sample sequence. The probe is often dual-labeled with a fluorescent molecule and a fluorescence quencher such that during the amplification process signal is generated through the release of the quenching molecule. Greater presence of sample results in greater amplification and thus greater and more rapid production of signal.

Sequence-specific nucleic acid hybridization assays are used for the detection of specific genetic sequences as indicators of genetic anomalies, mutations, and disease propensity. In addition, they are used for the detection of various biological agents and infectious pathogens. Because a complementary probe is required to detect the sequence of interest, nucleic acid sequencing techniques can rapidly determine the sequence of the probe being used in the assay and consequently the identity of the sequence of interest. The ability to reverse engineer a nucleic acid assay in this manner makes it easy to copy or circumvent the assay.

The ability to impede reverse engineering of nucleic acid hybridization assays would be highly valuable in a variety of circumstances. One example is protection from industrial espionage. Many of the sequences being used for medical diagnostic procedures as well as pathogen detection are part of the public domain; thus, it can be difficult for a company to maintain protection for the intellectual property produced from the utilization of specific sequences for diagnostic purposes. This is especially true in those foreign countries where little regard may be shown for any intellectual property protection. Thus, the only protection that companies have from industrial espionage through reverse engineering is keeping the specific sequences used for detection as a trade secret. Again, with the advances in nucleic acid technologies it is very easy and rapid to determine the sequences being used for nearly any detection platform, which allows a very rapid reproduction of specific assays.

Another situation in which it is desirable to impede reverse engineering of nucleic acid hybridization assays is the detection of agents for bioterrorism and biowarfare. In the case of bioterrorism and biowarfare, a primary concern is the presence of false positive samples (positive detection of the agent when the agent is not present) or false negatives (no detection of the agent when the agent is present).

A false positive sample, requires a similar involvement of first responders, medical staff, and a potential quarantine of the affected area as would be required for an actual attack. In the military a false positive can force troops to dress in biowarfare suits. Both responses cost money and diminish the availability and potency of the first responders and troops.

A false negative permits a real biological event to escape detection until significant symptomology occurs. This provides a chance for significant spread of an agent prior to detection and quarantine.

Because a false positive produces the same terror effect as a true positive sample and a false negative allows undetected spread of an agent, a detection platform must produce results with as much certainty as possible with as low as possible false positive and false negative results.

From a terrorist's perspective there are a number of ways to produce samples or agents that will result in a false positive or a false negative that directly relates to the detection system being used. Most nucleic acid detection platforms utilize a small unique DNA sequence to detect the presence or the absence of a gene that is indicative of a specific agent. However, if a terrorist became informed of the specific sequence that a detection platform uses for agent detection, a number of techniques could be used to produce false positive or false negative samples. Because the detection of an agent relies on the presence of that sequence but not necessarily the entire organism, introduction into a sample of a synthetic DNA sequence complementary to the nucleic acid probe being used for detection would produce the same result as if the entire organism was present.

In the same respect, to produce a false negative, the terrorist, knowing the detection sequence, could produce silent mutations in the organism that would change the detection sequence without changing the function of the gene product or the organism. Thus, the pathogenicity of the organism would not change, but the exquisite specificity of the detection platform would not indicate a positive sample since the detecting sequence in the organism had been changed.

Because of advances in nucleic acid technologies it is very easy and rapid to determine the sequences that are being used for nearly any detection platform; therefore, allowing false positive and false negative samples to be readily generated.

Clearly there is a need for methods to inhibit the reverse engineering of nucleic-acid based assays to protect intellectual property interest and to reduce the ability of a person to design a false-positive or false-negative agent to exploit a particular assay.

SUMMARY OF THE INVENTION

The present invention provides novel methods and compositions for inhibiting the identification of nucleic acid sequences used for the detection of specific nucleic acids. Thus, the invention is useful for protecting intellectual property interests in nucleic acid based assays. In addition, the invention will reduce or impede a person's ability to design a false-positive or false-negative agent to exploit a nucleic acid based assay.

In one embodiment, the invention provides a method of masking the identity of a detection sequence on a nucleic acid molecule comprising: obtaining a detection nucleic acid molecule comprising a known detection sequence; and associating with the detection nucleic acid molecule at least a first masking nucleic acid molecule comprising a first masking sequence, wherein the masking sequence varies from the detection sequence at one or more positions and thereby masks the identity of the detection sequence.

In another embodiment, the invention provides a method of masking the identity of a detection sequence on a nucleic acid molecule comprising: obtaining a detection nucleic acid molecule comprising a known detection sequence; associating with the nucleic acid molecule at least a first masking nucleic acid molecule comprising a first masking sequence, wherein the masking sequence varies from the detection sequence at one or more positions and thereby masks the identity of the detection sequence; and associating with the detection nucleic acid molecule and the first masking nucleic acid molecule at least a second masking nucleic acid molecule, wherein the second masking nucleic acid molecule comprises a second masking sequence that varies from the detection sequence and the first masking sequence at one or more positions.

In other embodiments, the invention provides a method of masking the identity of a detection sequence on a nucleic acid molecule comprising: obtaining a detection nucleic acid molecule comprising a known detection sequence; associating with the nucleic acid molecule at least a first masking nucleic acid molecule comprising a first masking sequence, wherein the masking sequence varies from the detection sequence at one or more positions and thereby masks the identity of the detection sequence; associating with the detection nucleic acid molecule and the first masking nucleic acid molecule at least a second masking nucleic acid molecule, wherein the second masking nucleic acid molecule comprises a second masking sequence that varies from the detection sequence and the first masking sequence at one or more positions; and associating with the detection nucleic acid molecule and the first and second masking nucleic acid molecules at least a third masking nucleic acid molecule, wherein the third masking nucleic acid molecule comprises a third masking sequence that varies from the detection sequence and the first and second masking sequences at one or more positions.

In certain aspects of the invention, the masking sequence varies from the detection sequence at 1, 2, 3, 4, 5, 6, 7, 8, 9, 10, 11, 12, 13, 14, 15, 16, 17, 18, 19, 20, 21, 22, 23, 24, 25, or more positions up to the total number of positions in the detection sequence. In certain embodiments the masking sequence varies from the detection sequence at 10%, 20%, 30%, 40%, 50%, 60%, 70%, 80%, 90%, or 100% of the positions in the detection sequence. In a preferred embodiment, the masking sequence varies from the detection sequence at at least half of the positions. More preferably, the masking sequence varies from the detection sequence at all positions.

In certain embodiments, the detection sequence is comprised within a hybridization probe. In certain embodiments the hybridization probe is labeled. In some embodiments, the detection sequence is comprised within a primer. In certain embodiments the primer is labeled. In certain embodiments, the detection sequence is comprised within a molecular imprint. In certain embodiments the molecular imprint is labeled. In some embodiments, the target sequence is labeled.

A number of different labels may be used in the present invention such as fluorophores, chromophores, radiophores, enzymatic tags, antibodies, chemiluminescence, electroluminescence, and affinity labels. One of skill in the art will recognize that these and other labels not mentioned herein can be used with success in this invention.

Examples of affinity labels include, but are not limited to the following: an antibody, an antibody fragment, a receptor protein, a hormone, biotin, DNP, a molecular imprint, or any polypeptide/protein molecule that binds to an affinity label.

Examples of enzyme tags include enzymes such as urease, alkaline phosphatase or peroxidase to mention a few. Colorimetric indicator substrates can be employed to provide a detection means visible to the human eye or spectrophotometrically, to identify specific hybridization with complementary nucleic acid-containing samples. All of these examples are generally known in the art and the skilled artisan will recognize that the invention is not limited to the examples described above.

Examples of fluorophores include, but are not limited to the following: all of the Alexa Fluor® dyes, AMCA, BODIPY® 630/650, BODIPY® 650/665, BODIPY®-FL, BODIPY®-R6G, BODIPY®-TMR, BODIPY®-TRX, Cascade Blue®, CyDyes™, including but not limited to Cy2™, Cy3™, and Cy5™, DNA intercalating dyes, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, and Texas Red®.

In certain embodiments, the invention provides methods for determining the nucleotide sequence of the masking sequence(s). In a preferred embodiment the nucleotide sequence of the masking sequence(s) are determined using an algorithm. More preferably, the nucleotide sequence of the masking sequence(s) are determined using an algorithm, wherein Masking Sequence 1 contains complementary nucleotides to the detection sequence at nucleotide position 1 and every third nucleotide thereafter, Masking Sequence 2 contains complementary nucleotides to the detection sequence at nucleotide position 2 and every third nucleotide thereafter, and Masking Sequence 3 contains complementary nucleotides to the detection sequence at nucleotide position 3 and every third nucleotide thereafter.

In some aspects of the invention, the detection nucleic acid molecule and the masking nucleic acid molecule(s) are combined on a solid support. Alternatively, a target nucleic acid molecule may be immobilized on a solid support. Non-limiting examples of solid supports include: nitrocellulose, nylon membrane, glass, activated quartz, activated glass, polyvinylidene difluoride (PVDF) membrane, polystyrene substrates, polyacrylamide-based substrate, other polymers, copolymers, or crosslinked polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules). A solid support may be in the form of, for example, a bead, a column, or a chip.

In one embodiment, the invention provides methods of performing a hybridization reaction comprising the steps of: obtaining a hybridization probe, which comprises a detection sequence designed to hybridize to a target sequence; providing a masking nucleic acid molecule that comprises a masking sequence, wherein the masking sequence of the masking nucleic acid molecule varies from the detection sequence at one or more positions, and further wherein the masking nucleic acid molecule has a reduced ability or inability to hybridize to the target sequence; and performing a hybridization reaction comprising the hybridization probe and the masking nucleic acid molecule in the presence of the target sequence under conditions permitting the selective hybridization of the hybridization probe to the target sequence.

In another embodiment, the invention provides methods of performing a hybridization reaction comprising the steps of: obtaining a hybridization probe, which comprises a detection sequence designed to hybridize to a target sequence; providing a first masking nucleic acid molecule that comprises a first masking sequence, wherein the masking sequence of the first masking nucleic acid molecule varies from the detection sequence at one or more positions, and further wherein the first masking nucleic acid molecule has a reduced ability or inability to hybridize to the target sequence; providing a second masking nucleic acid molecule comprising a second masking sequence that varies from the detection sequence and the first masking sequence at one or more positions, wherein the second masking nucleic acid molecule has a reduced ability or inability to hybridize to the target; and performing a hybridization reaction comprising the hybridization probe, the first masking nucleic acid molecule, and the second masking nucleic acid molecule in the presence of the target sequence under conditions permitting the selective hybridization of the hybridization probe to the target sequence.

In yet another embodiment, the invention provides methods of performing a hybridization reaction comprising the steps of: obtaining a hybridization probe, which comprises a detection sequence designed to hybridize to a target sequence; providing a first masking nucleic acid molecule that comprises a first masking sequence, wherein the masking sequence of the first masking nucleic acid molecule varies from the detection sequence at one or more positions, and further wherein the first masking nucleic acid molecule has a reduced ability or inability to hybridize to the target sequence; providing a second masking nucleic acid molecule comprising a second masking sequence that varies from the detection sequence and the first masking sequence at one or more positions, wherein the second masking nucleic acid molecule has a reduced ability or inability to hybridize to the target; providing a third masking nucleic acid molecule comprising a third masking sequence that varies from the detection sequence and the first and second masking sequences at one or more positions, wherein the third masking nucleic acid molecule has a reduced ability or inability to hybridize to the target; and performing a hybridization reaction comprising the hybridization probe, the first masking nucleic acid molecule, the second masking nucleic acid molecule, and the third masking nucleic acid molecule in the presence of the target sequence under conditions permitting the selective hybridization of the hybridization probe to the target sequence.

In certain aspects of the invention, the masking sequence varies from the detection sequence at 1, 2, 3, 4, 5, 6, 7, 8, 9, 10, 11, 12, 13, 14, 15, 16, 17, 18, 19, 20, 21, 22, 23, 24, 25, or more positions up to the total number of positions in the detection sequence. In certain embodiments the masking sequence varies from the detection sequence at 10%, 20%, 30%, 40%, 50%, 60%, 70%, 80%, 90%, or 100% of the positions in the detection sequence. In a preferred embodiment, the masking sequence varies from the detection sequence at at least half of the positions. More preferably, the masking sequence varies from the detection sequence at all positions.

The detection sequences and the masking sequences of the present invention may be of any length. In preferred embodiments the detection sequences and the masking sequences are from about 5 to about 100 nucleotides in length. More preferably, the detection sequences and the masking sequences are from about 10 to about 60 nucleotides in length. Even more preferably, the detection sequences and the masking sequences are 18 to 25 nucleotides in length. In certain embodiments, the detection sequences and the masking sequences are 18, 19, 20, 21, 22, 23, 24, or 25 nucleotides in length.

In some embodiments, the invention provides a composition comprising: a detection nucleic acid molecule comprising a known detection sequence; and a masking nucleic acid molecule comprising a masking sequence, wherein the masking sequence varies from the detection sequence at one or more positions and thereby masks the identity of the detection sequence.

In other embodiments, the invention provides a composition comprising: a detection nucleic acid molecule comprising a known detection sequence; a first masking nucleic acid molecule comprising a first masking sequence, wherein the first masking sequence varies from the detection sequence at one or more positions and thereby masks the identity of the detection sequence; and a second masking nucleic acid molecule, wherein the second masking nucleic acid molecule comprises a second masking sequence that varies from the detection sequence and the first masking sequence at one or more positions and thereby masks the identity of the detection sequence.

In certain embodiments, the invention provides a composition comprising: a detection nucleic acid molecule comprising a known detection sequence; a first masking nucleic acid molecule comprising a first masking sequence, wherein the first masking sequence varies from the detection sequence at one or more positions and thereby masks the identity of the detection sequence; a second masking nucleic acid molecule, wherein the second masking nucleic acid molecule comprises a second masking sequence that varies from the detection sequence and the first masking sequence at one or more positions and thereby masks the identity of the detection sequence; and a third masking nucleic acid molecule, wherein the third masking nucleic acid molecule comprises a third masking sequence that varies from the detection sequence and the first and second masking sequences at one or more positions and thereby masks the identity of the detection sequence.

In some aspects, the invention provides a composition wherein the detection nucleic acid molecule and the masking nucleic acid molecule(s) are combined on a solid support.

In certain aspects of the invention, the detection nucleic acid molecule further comprises an equilibrium sequence and the masking nucleic acid molecule(s) further comprises an equilibrium sequence. The equilibrium sequences equalize the mass and charge of the detection nucleic acid molecule and the masking nucleic acid molecule(s). An equilibrium sequence may be placed anywhere in the nucleic acid molecule. For example, the equilibrium sequence may be placed either 5' or 3' of the detection sequence or the masking sequence.

The identification of a detection sequence can also be inhibited by including many sequences of differing lengths in many different ratios along with the detection molecule. These different-length fragments (some shorter and some longer than the detection molecule) would further serve to complicate any sequencing efforts to reverse engineer the specific detection molecule. In particular, these different-length nucleic acid molecules would complicate mass spectrometry based sequencing methods. As used herein, the different-length nucleic acid molecules are also referred to as "decoy sequences" or "decoy molecules." As long as a sufficient amount of detection molecule is present in each assay in order to detect the sequence of interest any number of "decoy sequences" of any length could be added to the assay. In some embodiments, non-natural DNA molecules (i.e., PNA) are used. Due to their increased affinity for hybridization and thus, greater sensitivity, non-natural DNA molecules could increase the number of decoy sequences used per reaction. In certain aspects of the invention, decoy sequences are included in addition to masking sequences in order to inhibit the identification of the detection sequence.

The present invention also provides kits. In one embodiment, the present invention provides a kit comprising a detection nucleic acid molecule and a masking nucleic acid molecule in a suitable container means. In certain embodiments, the kit comprises a detection nucleic acid molecule and two or more masking nucleic acid molecules in a suitable container means. In some embodiments, the detection nucleic acid molecule and masking nucleic acid molecule(s) are coupled to a solid support such as a microsphere. In other embodiments, the kit comprises a detection nucleic acid molecule and one or more decoy molecules in a suitable container means.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows a Luminex® xMAP® microsphere 1 coupled covalently to a unique detection nucleic acid molecule 2. A labeled target nucleic acid molecule 3 will hybridize to the complementary detection nucleic acid molecule and be "captured" on the microsphere. The labeled target nucleic acid molecule hybridized to the detection nucleic acid molecule is shown in FIG. 1B. FIG. 1C shows a Luminex microsphere 1 coupled covalently to a unique detection nucleic acid molecule 2, and a labeled target nucleic acid molecule 3 hybridized to the detection nucleic acid molecule. Also shown in FIG. 1C are three different masking nucleic acid molecules 4, 5, and 6 coupled to the microsphere.

FIG. 2A and FIG. 2B. FIG. 2A and FIG. 2B show that the Luminex xMAP system can capture and detect a target oligonucleotide on beads coupled with a detection nucleic acid molecule and one, two, or three masking nucleic acid molecules. In FIG. 2A, fluorescent intensity is plotted on the y axis, and the concentration of the target molecule in attomoles is shown on the x axis. Increased fluorescent intensity indicates increased hybridization of the target sequence to the detection sequence. The ability of the target sequence to hybridize to the detection sequence was assayed on beads coupled to: Detection Molecule alone, Detection Molecule+1 Masking Molecule, Detection Molecule+2 Masking Molecules, and Detection Molecule+3 Masking Molecules. FIG. 2B shows in table format the same data as in FIG. 2A.

FIG. 3A and FIG. 3B. FIG. 3A and FIG. 3B show the same assay as in FIG. 2A and FIG. 2B, but using a signal amplification process and assay sensitivity optimization. The signal amplification and sensitivity optimization allows approximately 100-fold greater sensitivity.

FIG. 4A and FIG. 4B. FIG. 4A and FIG. 4B show the capture and detection of three target sequences generated by PCR™ amplification of human patient DNA samples (two known positive samples and one known negative sample) by Luminex beads coupled with a detection nucleic acid molecule and one, two, or three masking nucleic acid molecules. In FIG. 4A, fluorescent intensity is plotted on the y axis, and the PCR™ amplicon samples are shown on the x axis. Increased fluorescent intensity indicates increased hybridization of the PCR™ amplicon sequence to the detection sequence. The ability of the PCR™ amplicon sequence to hybridize to the detection sequence was assayed on beads coupled to: Detection Molecule alone, Detection Molecule+1 Masking Molecule, Detection Molecule+2 Masking Molecules, and Detection Molecule+3 Masking Molecules. FIG. 4B shows in table format the same data as in FIG. 4A.

FIG. 5A and FIG. 5B. FIG. 5A and FIG. 5B show the capture and detection of three target sequences amplified by PCR™ from human patient samples (two known positive samples and one known negative sample) with a primer set and one, two, or three masking primer sets by Luminex beads coupled with a detection molecule. In FIG. 5A, fluorescent intensity is plotted on the y axis, and the PCR™ amplicon samples are shown on the x axis. Increased fluorescent intensity indicates increased hybridization of the PCR™ amplicon sequence to the detection sequence. The ability of the PCR™ primers to amplify using a single Primer Set, a Primer Set+1 Masking Primer Set, a Primer Set+2 Masking Primer Sets, and a Primer Set+3 Masking Primer Sets was assayed on beads coupled to the detection molecule. FIG. 5B shows in table format the same data as in FIG. 5A. As demonstrated in FIG. 5A and FIG. 5B, there was no reduction in hybridization signal generated from amplicons produced with a specific primer set alone or amplicons produced with a specific primer set plus one, two, or three masking primer sets.

DESCRIPTION OF ILLUSTRATIVE EMBODIMENTS

A. The Present Invention

Figure 1B:
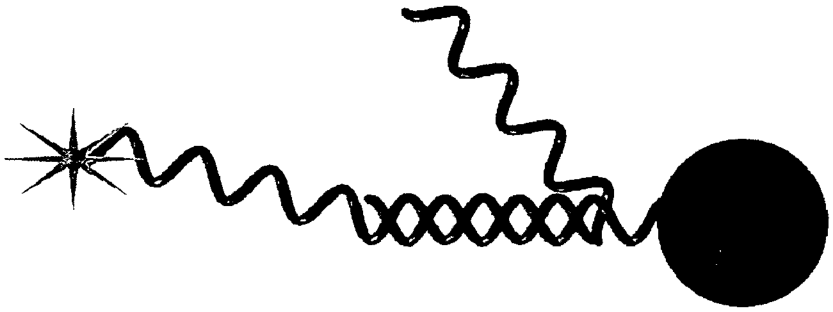
FIG. 1A, FIG. 1B, and FIG. 1C.

Sequence-specific nucleic acid hybridization assays are used for the detection of specific genetic sequences as indicators of genetic anomalies, mutations, and disease propensity. In addition, they are used for the detection of various biological agents and infectious pathogens. Because a complementary probe is required to detect a sequence of interest in a hybridization-based assay, nucleic acid sequencing techniques can rapidly determine the specific probe sequence being used for detection. This allows reverse engineered assays to be produced rapidly. In addition, it enables the circumvention of hybridization-based assays for biological agent or infectious pathogen detection by providing the information necessary to create or alter nucleic acid sequences to produce false positives or false negatives.

The present invention provides methods and compositions for inhibiting the identification of detection sequences. More specifically, the invention provides masking sequences that mask the identity of detection sequences. In a preferred embodiment, the invention provides a method of masking the identity of a detection sequence on a nucleic acid molecule comprising: obtaining a detection nucleic acid molecule comprising a known detection sequence; associating with the nucleic acid molecule three masking nucleic acid molecules comprising three masking sequences, wherein the masking sequences vary from the detection sequence and from each other at all base positions and thereby mask the identity of the detection sequence by confounding DNA sequence analysis.

A "detection sequence" is a nucleic acid sequence capable of hybridizing to a specific nucleic acid sequence of interest; and thus enables, for example, the detection, capture, isolation, or amplification of the specific nucleic acid. A "detection sequence" may be comprised within a "detection nucleic acid molecule." A "detection nucleic acid molecule" is also referred to as a "detection molecule." In addition to comprising a "detection sequence," a "detection nucleic acid molecule" may comprise additional elements. These additional elements may be, for example, additional nucleic acids or labels. A "detection sequence" may be a hybridization probe or a primer, or it may be comprised within a hybridization probe or a primer. Likewise, a "detection nucleic acid molecule" may be a hybridization probe or a primer.

A "masking sequence" is a sequence that masks the identity of a detection sequence. A "masking sequence" may be comprised within a "masking nucleic acid molecule." A "masking nucleic acid molecule" is also referred to as a "masking molecule," a "masking primer set," a "masking sequence primer set," or a "masking sequence primer." In addition to comprising a masking sequence, a masking nucleic acid molecule may comprise additional elements. These additional elements may be, for example, additional nucleic acids or labels or other similar or related molecules.

One feature of a masking sequence is that it is the same length as the detection sequence that it is masking. Or, where the masking sequence and detection sequence are comprised within a masking nucleic acid molecule and a detection nucleic acid molecule, respectively, the masking nucleic acid molecule and the detection nucleic acid molecule are the same length. Making the masking nucleic acid molecule and the detection nucleic acid molecule the same length prevents the isolation of one molecule from the other by conventional techniques used by those skilled in the art to separate nucleic acids based on size. In addition, labels present in a detection nucleic acid molecule that could be used to isolate or identify the molecule, should also be present in the masking nucleic acid molecule. For example, if the detection nucleic acid molecule is biotinylated, the masking nucleic acid molecule should be biotinylated to prevent the selective isolation of the detection nucleic acid molecule.

Another feature of a masking sequence is that its nucleic acid sequence varies from that of the detection sequence at one or more positions. In a preferred embodiment, the masking sequence varies from the detection sequence at every nucleotide position. Although it is preferred that a masking sequence varies from the detection sequence at every base position, this is not always necessary, as DNA sequencing analysis may still be confounded if there are identical bases at some positions.

Preferably, three masking sequences are used, which have masking sequences that vary from not only the detection sequence, but also from each other. Upon DNA sequence analysis, the presence of the masking sequences would produce a nonsensical nucleotide sequence at each base position. The inclusion of a detection sequence and three masking sequences that vary from each other at every base position increases the possible sequences present to $4^y$ different combinations, where y is the number of bases in the specific detection sequence. In the case of a 22-mer oligonucleotide, this represents over $10^{13}$ possibilities.

Each masking sequence can be screened against available genome databases, such as GenBank, to ensure that it will not hybridize to a sequence in the sample of interest or if it can hybridize to a specific sequence it only does so at a significantly lower affinity than the detection sequence and the sequence of interest. In the event that there is a sequence in the sample to which a particular masking sequence will hybridize, that masking sequence can be excluded from the assay or an alternate set of masking sequences can be generated that will not hybridize to a known sequence in the sample. Excluding one of the three masking sequences reduces the possible combinations of sequences from $4^y$ possibilities to $3^y$ possibilities. In the case of a 22-mer oligonucleotide, this would still provide over $10^{10}$ possibilities. Even under circumstances where only one masking sequence is used, there would still be 4,194,304 possible combinations for a 22-mer oligonucleotide.

The nucleotide sequence of the masking sequence(s) may be determined using an algorithm. For example, to generate 3 masking sequences that differ from the detection sequence at every position one could begin by designing Masking Sequence 1 to have complementary nucleotides to the detection sequence at nucleotide position 1 and every third nucleotide thereafter, Masking Sequence 2 to have complementary nucleotides to the detection sequence at nucleotide position 2 and every third nucleotide thereafter, and Masking Sequence 3 to have complementary nucleotides to the detection sequence at nucleotide position 3 and every third nucleotide thereafter. This initial step in designing masking sequences is illustrated below in Table 1.

TABLE 1

| Base Position | 5' 1 | 2 | 3 | 4 | 5 | 3' 6 |
|---|---|---|---|---|---|---|
| Detection Sequence | T | T | G | T | C | A |
| Masking Sequence 1 | **A** | | | **A** | | |
| Masking Sequence 2 | | **A** | | | **G** | |
| Masking Sequence 3 | | | **C** | | | **T** |

The next step in designing the masking sequences is the vertical filling of the first available masking sequence position using a nucleotide designated in Table 2.

TABLE 2

| Detection Sequence Base | Masking Sequence Base |
|---|---|
| A | G |
| T | C |
| G | T |
| C | A |

The result of the vertical filling of the first available masking sequence position shown in Table 1 using a nucleotide designated in Table 2 is shown below in Table 3. The newly added masking sequence bases are in italics.

TABLE 3

| Base Position | 5' 1 | 2 | 3 | 4 | 5 | 3' 6 |
|---|---|---|---|---|---|---|
| Detection Sequence | T | T | G | T | C | A |
| Masking Sequence 1 | **A** | *C* | *T* | **A** | *A* | *G* |
| Masking Sequence 2 | C | **A** | | *C* | **G** | |
| Masking Sequence 3 | | | **C** | | | **T** |

The final step in designing the masking sequences is the vertical filling of the remaining available position for each masking sequence position using a nucleotide designated in Table 4.

TABLE 4

| Detection Sequence Base | Masking Sequence Base |
|---|---|
| A | C |
| T | G |
| G | A |
| C | T |

The result of the vertical filling of the remaining available position for each masking sequence position shown in Table 3 using a nucleotide designated in Table 4 is shown below in Table 5. The newly added masking sequence bases are underlined.

TABLE 5

| Base Position | 5' 1 | 2 | 3 | 4 | 5 | 3' 6 |
|---|---|---|---|---|---|---|
| Detection Sequence | T | T | G | T | C | A |
| Masking Sequence 1 | **A** | *C* | *T* | **A** | *A* | *G* |
| Masking Sequence 2 | *C* | **A** | A | *C* | **G** | C |
| Masking Sequence 3 | G | G | **C** | G | T | T |

In the example shown in Table 5, the detection sequence is 6 nucleotides in length and has a sequence of 5'-TTGTCA-3'. The detection sequence would specifically hybridize to a target sequence having the complementary sequence of 5'-TGACAA-3'. Also shown in Table 5 are 3 masking sequences. Each masking sequence is identical in length to the detection sequence. In addition, the sequence of each masking sequence varies from the sequence of the detection sequence at each base position. The masking sequences also vary from each other at each base position. Thus, for example, the first base of the detection sequence is T, the first base of Masking Sequence 1 is A, the first base of Masking Sequence 2 is C, and the first base of Masking Sequence 3 is G. Therefore, if attempts were made to sequence the 6-base long detection sequence in the presence of the 3 6-base long masking sequences, the sequence data would be nonsensical showing an A, T, G, and C at every position.

The masking sequences of the present invention are designed to provide a mixture of nucleic acid sequences (a detection sequence and one or more masking sequences) whereby standard sequencing techniques will not reveal a specific unique sequence. However, because few nucleotide sequences are represented by equal numbers of each nucleotide, there likely will exist a discernable difference in both charge and mass between the detection nucleic acid molecule and each of the masking nucleic acid molecules. The recent integration of on-line high-performance liquid chromatography (HPLC) purification of nucleic acid fragments and mass spectrometry analysis provides a powerful tool for the determination of a specific sequence of sample DNA. Significantly, these methods have an exquisite ability to separate short nucleotide sequences based on both charge and mass.

An "equilibrium sequence" can be used to prevent the separation of the detection nucleic acid molecule from a masking nucleic acid molecule based on differences in charge and mass. Thus, in certain aspects of the invention, the detection nucleic acid molecule and masking nucleic acid molecule may comprise an "equilibrium sequence." "Equilibrium sequences" are sequences included in the detection nucleic acid molecule and masking nucleic acid molecules to ensure that the molecules comprise an equal proportion of each nucleotide such that each nucleic acid molecule is of equal mass and charge. The addition of equilibrium sequences will complicate attempts to isolate and sequence the detection sequence using methods such as HPLC and mass spectrometry.

An algorithm can be generated to determine an appropriate equilibrium sequence for the detection molecule and the masking molecule(s). For example, the following algorithm can be used to determine the number of equilibrium nucleotides required to be added to each molecule to equilibrate mass and charge:

$$\text{equilibrium nucleotides} = (4 \times \text{the maximally represented nucleotide in any one of the molecules}) - (\text{the number of total bases in the detection nucleic acid molecule})$$

For example, if adenine is the most abundant nucleotide in any one of the detection nucleic acid molecule and the masking nucleic acid molecule(s), and it is represented 9 times in a 22 nucleotide sequence, then an equilibrium sequence length of $(4 \times 9) - 22$ or 14 nucleotides would be required.

Tables 6A to 6D further illustrate the design of equilibrium sequences. Table 6A shows the sequence of a detection molecule and three masking molecules. The base composition of each molecule is shown on the right side of the table. For example, the detection molecule is composed of 1 adenine, 0 cytosines, 1 guanine, and 5 thymines.

TABLE 6A

Base Compositions of Detection Molecule and Three Masking Molecules.

| | 5' 1 | 2 | 3 | 4 | 5 | 6 | 3' 7 | Base Composition A | C | G | T |
|---|---|---|---|---|---|---|---|---|---|---|---|
| Detection Molecule | T | T | T | A | T | T | G | 1 | 0 | 1 | 5 |
| Masking Molecule 1 | A | C | C | T | C | C | C | 1 | 5 | 0 | 1 |
| Masking Molecule 2 | C | A | G | G | A | G | T | 2 | 1 | 3 | 1 |
| Masking Molecule 3 | G | G | A | C | G | A | A | 3 | 1 | 3 | 0 |

As can be seen in Table 6A, the molecules are 7 nucleotides in length and the maximum number of any one nucleotide in any one molecule is 5. Thus, using the algorithm described above, the equilibrium nucleotide sequence length is calculated to be (4×5)−7=13.

In addition to determining the length of the equilibrium sequence, its nucleotide composition must also be determined. The number of each nucleotide needed to equilibrate the mass and charge of each molecule is equal to the maximum number of any one base in any one molecule minus the individual nucleotide composition for that molecule. The result being that each nucleotide is represented equally across all of the molecules. Continuing with the example from Table 6A, in which the maximum number of any one base in any one molecule is 5, Table 6B shows the number of each nucleotide needed by each equilibrium sequence to equilibrate the mass and charge among the four molecules. For example, looking specifically at the detection molecule in Table 6B, it can be seen the equilibrium sequence should be composed of 4 adenines, 5 cytosines, 4 guanines, and 0 thymines. The result being that the equilibrated detection molecule will be composed of an equal number of each nucleotide, specifically 5 adenines, 5 cytosines, 5 guanines, and 5 thymines.

TABLE 6B

Nucleotide Composition of Each Equilibrium Sequence.

| | Number of Each Base Needed for Equilibrium | | | |
|---|---|---|---|---|
| | A | C | G | T |
| Detection Molecule | 5 − 1 = 4 | 5 − 0 = 5 | 5 − 1 = 4 | 5 − 5 = 0 |
| Masking Molecule 1 | 5 − 1 = 4 | 5 − 5 = 0 | 5 − 0 = 5 | 5 − 1 = 4 |
| Masking Molecule 2 | 5 − 2 = 3 | 5 − 1 = 4 | 5 − 3 = 2 | 5 − 1 = 4 |
| Masking Molecule 3 | 5 − 3 = 2 | 5 − 1 = 4 | 5 − 3 = 2 | 5 − 0 = 5 |

TABLE 6C

Nucleotide Sequence for Equilibrium Sequences.

| | 5' 1 | 2 | 3 | 4 | 5 | 6 | 7 | 8 | 9 | 10 | 11 | 12 | 3' 13 |
|---|---|---|---|---|---|---|---|---|---|---|---|---|---|
| Detection Molecule (SEQ ID NO: 1) | A | C | G | A | C | G | A | C | G | A | C | G | C |
| Masking Molecule 1 (SEQ ID NO: 2) | G | T | A | G | T | A | G | T | A | G | T | A | G |
| Masking Molecule 2 (SEQ ID NO: 3) | C | G | T | C | A | T | C | G | C | T | A | T | A |
| Masking Molecule 3 (SEQ ID NO: 4) | T | A | C | T | G | C | T | A | T | C | G | C | T |

The equilibrium sequence can be placed anywhere within the detection nucleic acid molecule or the masking nucleic acid molecule, so long as it does not disrupt the detection sequence or the masking sequence. In Table 6D, the equilibrium sequence is at the 5' end of the detection molecule or masking molecule. However, the equilibrium sequence could have been placed at the 3' end or anywhere within the detection molecule or masking molecule, so long as it did not disrupt the detection sequence or the masking sequence.

TABLE 6D

Complete Nucleotide Sequences.

| | | Equilibrium Sequence | | | | | | | | | | | | | Detection or Masking Molecule | | | | | | | |
|---|---|---|---|---|---|---|---|---|---|---|---|---|---|---|---|---|---|---|---|---|---|---|
| | 5' | 1 | 2 | 3 | 4 | 5 | 6 | 7 | 8 | 9 | 10 | 11 | 12 | 13 | 14 | 15 | 16 | 17 | 18 | 19 | 20 | 3' |
| Detection Molecule (SEQ ID NO: 5) | | A | C | G | A | C | G | A | C | G | A | C | G | C | T | T | T | A | T | T | G | |
| Masking Molecule 1 (SEQ ID NO: 6) | | G | T | A | G | T | A | G | T | A | G | T | A | G | A | C | C | T | C | C | C | |
| Masking Molecule 2 (SEQ ID NO: 7) | | C | G | T | C | A | T | C | G | C | T | A | T | A | C | A | G | G | A | G | T | |
| Masking Molecule 3 (SEQ ID NO: 8) | | T | A | C | T | G | C | T | A | T | C | G | C | T | G | G | A | C | G | A | A | |

While the nucleotide composition of an equilibrium sequence is important, the order of the nucleotides is not important. Table 6C shows an equilibrium sequence for the detection molecule and each of the three masking molecules. Each equilibrium sequence was randomly generated based on the nucleotide composition indicated in Table 6B.

As can be seen in Table 6D, each complete 20 nucleotide sequence has an equal number of each nucleotide (i.e., 5 of each A, G, C, and T). Because the nucleotide composition is the same across all four molecules, the molecules have the same mass and charge. Therefore, the molecules shown in Table 6D could not be separated on the basis of length, mass, or charge. Consequently, attempts to sequence a mixture of these four nucleic acids would result in nonsensical sequence data.

Decoy sequences could also be used to confound attempts at sequencing via mass spectrometry. "Decoy sequences" are sequences of differing lengths (some shorter and some longer than the detection molecule) that may be included with the detection molecule. The decoy sequences may be included in the assay in many different ratios. As long as a sufficient amount of detection molecule exists in each assay to detect the sequence of interest, any number of decoy sequences of any length could be added to the assay. Non-natural DNA molecules (ie PNA) due to their increased affinity for hybridization and thus, greater sensitivity, could be utilized to increase the number of decoy sequences used per reaction. Decoy molecules may be used in addition to masking molecules to inhibit the identification of the detection sequence. It is also possible to use decoy molecules to inhibit the identification of the detection sequence in the absence of masking molecules.

As with masking sequences, each decoy sequence can be screened against available genome databases, such as GenBank, to ensure that it will not hybridize to a sequence in the sample of interest or if it can hybridize to a specific sequence it only does so at a significantly lower affinity than the detection sequence and the sequence of interest. In the event that there is a sequence in the sample to which a particular decoy sequence will hybridize, that decoy sequence can be excluded from the assay. In addition, labels present in a detection nucleic acid molecule that could be used to isolate or identify the molecule, should also be present in the decoy molecule.

B. Nucleic Acids

1. Preparation of Nucleic Acids

The detection sequences, masking sequences, and target sequences of the present invention may be prepared by any technique known to one of ordinary skill in the art, such as for example, chemical synthesis, enzymatic production, or biological production. In addition to being prepared by these methods, the masking sequences of the present invention may also be used to conceal the identity of the detection sequences (e.g., probes and primers) used in these methods. For example, masking sequences can be used to mask the identity of the primers used to amplify a target sequence.

Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

Nucleic acids used as a template for amplification may be isolated from cells, tissues or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A reverse transcriptase PCR™ amplification procedure may be performed to reverse transcribe mRNA into cDNA. Methods of RT-PCR are well known in the art (see Sambrook et al., 2001). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence, which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids, which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR™" (Frohman, 1990; Ohara et al., 1989).

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

Amplification products may be visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra. In another approach, a labeled nucleic acid probe is brought into contact with the amplified marker sequence, following separation of the amplification products. The probe may be conjugated to a chromophore, radiolabeled, or conjugated to a binding partner, such as an antibody or biotin.

One example of a detection method is Southern blotting and hybridization with a labeled probe. The techniques involved in Southern blotting are well known to those of skill in the art (see Sambrook et al., 2001). U.S. Pat. No. 5,279,721, incorporated by reference herein, discloses an apparatus and method for the automated electrophoresis and transfer of nucleic acids. The apparatus permits electrophoresis and blotting without external manipulation of the gel.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

2. Nucleic Acid Analogs

A nucleic acid of the present invention may comprise, or be composed entirely of, an analog of a naturally occurring nucleotide. As used herein an "analog" refers to a molecule that may or may not structurally resemble a naturally occurring molecule or moiety, but possesses similar functions.

Nucleotide analogs are well known in the art. A non-limiting example is a "peptide nucleic acid," also known as a "PNA," "peptide-based nucleic acid analog," or "PENAM," described in U.S. Pat. Nos. 5,786,461, 5,891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moiety that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

Another non-limiting example is a locked nucleic acid or "LNA." An LNA monomer is a bi-cyclic compound that is structurally similar to RNA nucleosides. LNAs have a furanose conformation that is restricted by a methylene linker that connects the 2'-O position to the 4'-C position, as described in Koshkin et al., 1998a and 1998b and Wahlestedt et al., 2000.

Yet another non-limiting example is a "polyether nucleic acid," described in U.S. Pat. No. 5,908,845, incorporated herein by reference. In a polyether nucleic acid, one or more nucleobases are linked to chiral carbon atoms in a polyether backbone.

3. Hybridization

Sequence-specific nucleic acid hybridization assays are used for the detection of specific genetic sequences as indicators of genetic anomalies, mutations, and disease propensity. In addition, they are used for the detection of various biological agents and infectious pathogens. As noted, because a complementary probe is required to detect the sequence of interest in a hybridization based assay, nucleic acid sequencing techniques can rapidly determine the sequence of the probe being used in the assay and consequently the identity of the sequence of interest. The ability to reverse engineer a nucleic acid assay in this manner makes it easy to copy or circumvent the assay. Thus, it is envisioned that the masking sequences of the present invention will be useful in preventing reverse engineering or circumvention of hybridization assays.

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridizes" or "capable of hybridizing" encompasses the terms "stringent conditions" or "high stringency" and the terms "low stringency" or "low stringency conditions."

As used herein "stringent conditions" or "high stringency" are those conditions that allow hybridization between or within one or more nucleic acid strands containing complementary sequences, but preclude hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acids, the length and nucleobase content of the target sequences, the charge composition of the nucleic acids, and to the presence or concentration of formamide, tetramethylammonium chloride or other solvents in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

The present invention may be employed in solution hybridization, as in PCR™, as well as in solid phase hybridization. The hybridization conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772.

4. Labels

To detect hybridization, it will be advantageous to employ nucleic acids in combination with an appropriate detection means. Recognition moieties incorporated into primers, incorporated into the amplified product during amplification, or attached to probes are useful in the identification of nucleic acid molecules. A number of different labels may be used for this purpose such as fluorophores, chromophores, radiophores, enzymatic tags, antibodies, chemiluminescence, electroluminescence, affinity labels, etc. One of skill in the art will recognize that these and other labels not mentioned herein can be used with success in this invention. As noted, when the detection nucleic acid molecule is labeled, it is generally desirable that the masking nucleic acid molecule(s) be similarly labeled to prevent separation of the detection nucleic acid molecule from the masking nucleic acid molecule(s) based on the presence or absence of the label.

Examples of affinity labels include, but are not limited to the following: an antibody, an antibody fragment, a receptor protein, a hormone, biotin, DNP, or any polypeptide/protein molecule that binds to an affinity label.

Examples of enzyme tags include enzymes such as urease, alkaline phosphatase or peroxidase to mention a few. Colorimetric indicator substrates can be employed to provide a detection means visible to the human eye or spectrophotometrically, to identify specific hybridization with complementary nucleic acid-containing samples. All of these examples are generally known in the art and the skilled artisan will recognize that the invention is not limited to the examples described above.

Examples of fluorophores include, but are not limited to the following: all of the Alexa Fluor® dyes, AMCA, BODIPY® 630/650, BODIPY® 650/665, BODIPY®-FL, BODIPY®-R6G, BODIPY®-TMR, BODIPY®-TRX, Cascade Blue®, CyDyes™, including but not limited to Cy2™, Cy3™, and Cy5™, DNA intercalating dyes, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, and Texas Red®.

5. Gene Chips and Microarrays

The present invention may be used to protect the identity of nucleic acid sequences used with DNA chips and microarrays.

DNA arrays and gene chip technology provide a means of rapidly screening a large number of nucleic acid samples for their ability to hybridize to a variety of single stranded DNA probes immobilized on a solid substrate. These techniques involve quantitative methods for analyzing large numbers of genes rapidly and accurately. The technology capitalizes on the complementary binding properties of single stranded DNA to screen DNA samples by hybridization (Pease et al. (1994); Fodor et al. (1991)). Basically, a DNA array or gene chip consists of a solid substrate upon which an array of single stranded DNA molecules have been attached. For screening, the chip or array is contacted with a single stranded DNA sample, which is allowed to hybridize under stringent conditions. The chip or array is then scanned to determine which probes have hybridized.

The present invention may be used to protect the identity of the nucleic acid probes immobilized on an array. For example, to protect the identity of a probe that is immobilized on a DNA chip or microarray, one or more masking sequences would also be immobilized on the DNA chip or microarray. By associating same-length masking sequences with a probe, attempts to sequence the probe would be impeded.

In circumstances where the target sequence is amplified prior to hybridization on a DNA chip or microarray, it is desirable to associate the masking sequences with the primers used in the amplification, such that attempts to sequence the primers is impeded by the presence of the masking sequences. Commonly, the primers used to amplify target sequences for DNA chip or microarray analysis also label the target nucleic acid with a substance that emits a detectable signal, for example, luminescence. Therefore, to prevent separation of the masking sequences from the primers based on the presence of a particular label, the masking sequences should have the same label as the primer.

The ability to directly synthesize on or attach polynucleotide probes to solid substrates is well known in the art. See U.S. Pat. Nos. 5,837,832 and 5,837,860, both of which are expressly incorporated by reference. A variety of methods have been utilized to either permanently or removably attach the probes to the substrate. Exemplary methods include: the immobilization of biotinylated nucleic acid molecules to avidin/streptavidin coated supports (Holmstrom, 1993), the direct covalent attachment of short, 5'-phosphorylated primers to chemically modified polystyrene plates (Rasmussen et al., 1991), or the precoating of the polystyrene or glass solid phases with poly-L-Lys or poly L-Lys, Phe, followed by the covalent attachment of either amino- or sulfhydryl-modified oligonucleotides using bi-functional crosslinking reagents (Running et al., 1990; Newton et al., 1993). When immobilized onto a substrate, the probes are stabilized and therefore may be used repeatedly. In general terms, hybridization is performed on an immobilized nucleic acid target or a probe molecule that is attached to a solid surface such as nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules.

6. Luminex Technology

In certain embodiments, the present invention is used in conjunction with Luminex® xMAP® technology. The Luminex technology allows the quantitation of nucleic acid products immobilized on fluorescently encoded microspheres. By dyeing microspheres with 10 different intensities each of two spectrally distinct fluorochromes, 100 fluorescently distinct populations of microspheres are produced. These individual populations (sets) can represent individual detection sequences and the magnitude of hybridization on each set can be detected individually. The magnitude of the hybridization reaction is measured using a third spectrally distinct fluorochrome called a reporter. The reporter molecule signals the extent of the reaction by attaching to the molecules on the microspheres. As both the microspheres and the reporter molecules are labeled, digital signal processing allows the translation of signals into real-time, quantitative data for each reaction. The Luminex technology is described, for example, in U.S. Pat. Nos. 5,736,330, 5,981,180, and 6,057,107, all of which are specifically incorporated by reference.

Figure 1A:
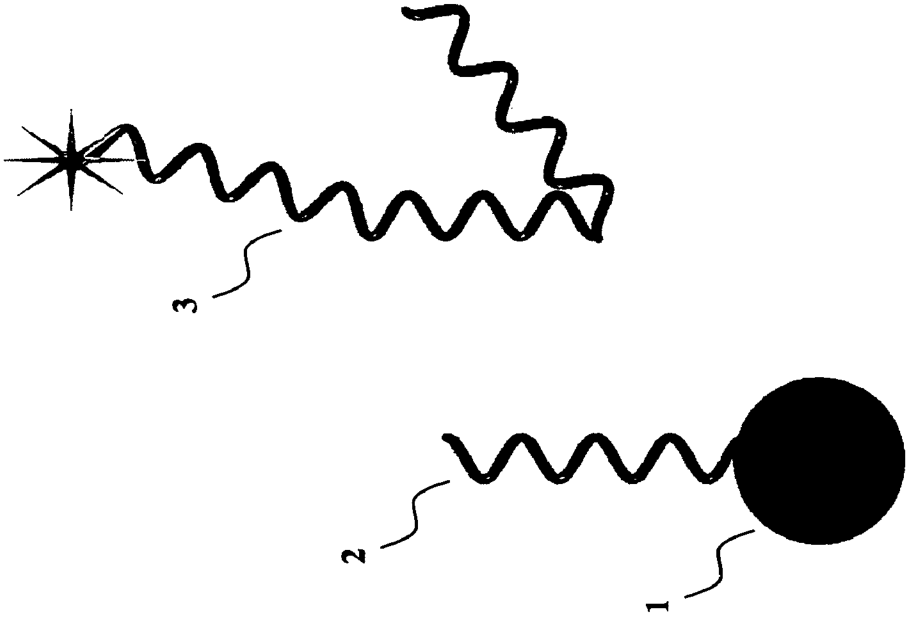

The use of the present invention in conjunction with the Luminex xMAP system may be more particularly described by reference to FIG. 1A, FIG. 1B, and FIG. 1C. FIG. 1A and FIG. 1B illustrate the Luminex xMAP system without masking sequences. FIG. 1A shows a microsphere with a unique fluorescent "bar code" 1 coupled covalently to a unique detection nucleic acid molecule 2. A labeled target nucleic acid molecule 3 will hybridize to the complementary detection nucleic acid molecule and be "captured" on the microsphere. The labeled target nucleic acid molecule hybridized to the detection nucleic acid molecule is shown in FIG. 1B. The target-associated label quantifies the hybridization reaction, and the fluorescent "bar code" of the microsphere identifies the detection sequence to which the target is hybridized.

Figure 1C:
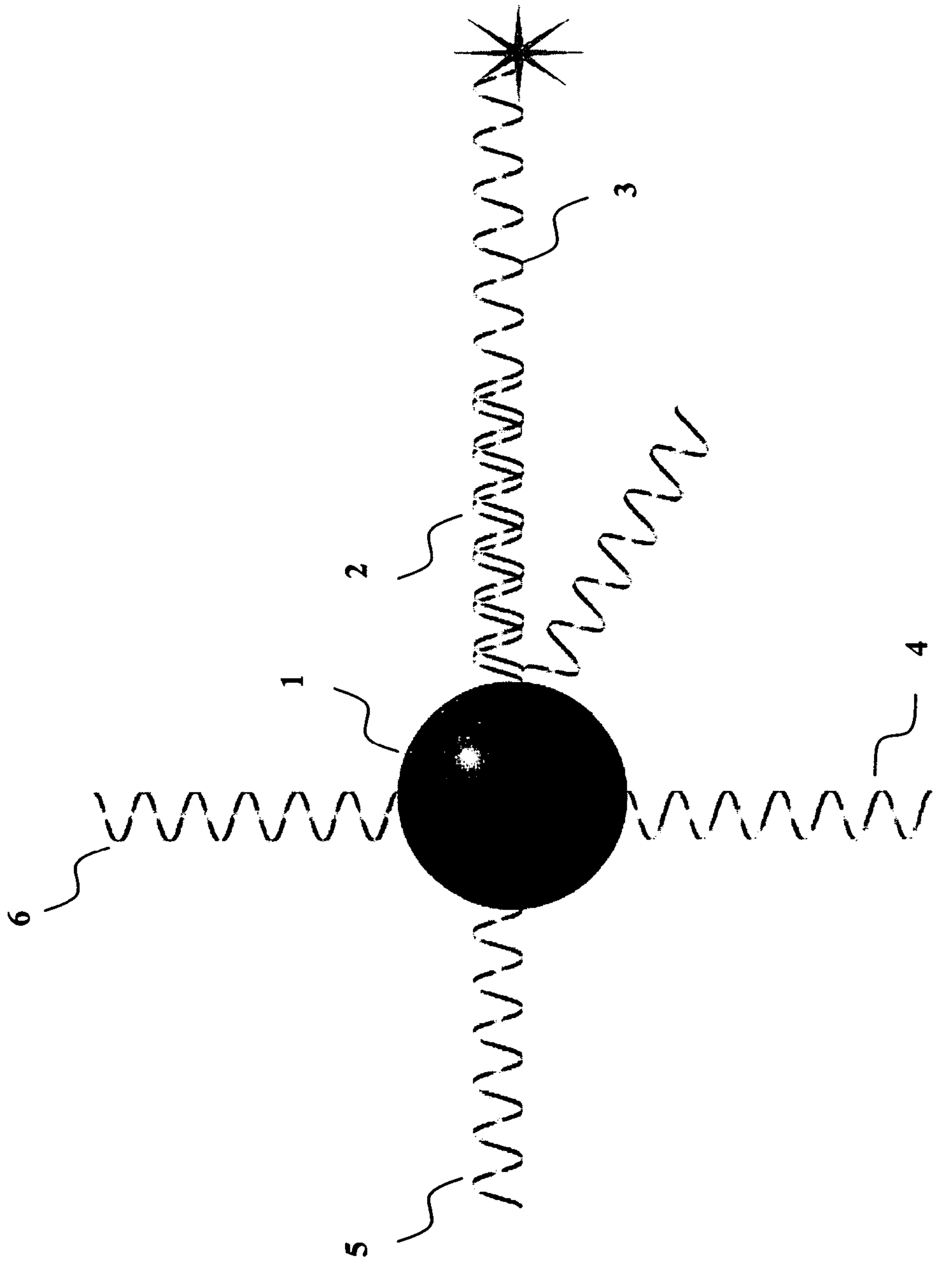

As in FIG. 1A and FIG. 1B, FIG. 1C shows a microsphere with a unique fluorescent "bar code" 1 coupled covalently to a unique detection nucleic acid molecule 2, and a labeled target nucleic acid molecule 3 hybridized to the detection nucleic acid molecule. Also shown in FIG. 1C are three different masking nucleic acid molecules 4, 5, and 6 coupled to the microsphere. The masking nucleic acid molecules are the same length as the detection nucleic acid molecule. In addition, the sequences of the three masking nucleic acid molecules differ from the detection nucleic acid molecule and from each other. As described above, the target-associated label quantifies the hybridization reaction, and the fluorescent "bar code" of the microsphere identifies the detection sequence to which the target is hybridized. The inventors have demonstrated that coupling three different masking nucleic acid molecules to the microsphere does no significantly inhibit the ability to detect hybridization between the detection nucleic acid sequence and the target nucleic acid sequence. However, attempts to identify the sequence of the probe (i.e., the detection nucleic acid sequence) would be impeded by the presence of the masking sequences.

In circumstances where the target sequence is amplified prior to hybridization on a microsphere, it is desirable to associate masking sequence sets with the primer sets used in the amplification, such that attempts to sequence the primer sets is impeded by the presence of the masking sequence sets. Commonly, the primer sets used to amplify target sequences for microsphere analysis also label the target nucleic acid. Therefore, to prevent separation of the masking sequence sets from the primer sets based on the presence of a particular label, the masking sequence sets should have the same label as the primer sets. For example, if the target sequence (i.e., reporter molecule) is amplified using biotinylated primer sets, the masking sequence sets should also be biotinylated.

7. Competitive Binding Assay

The present invention may also be used in conjunction with a competitive binding assay format. In general, this format involves a detection sequence comprised within a detection molecule, which is coupled to a solid surface, and a labeled sequence complementary to the detection sequence in solution. With this format, the target sequence in the sample being assayed does not need to be labeled. Rather, the target sequence's presence in the sample is detected because it competes with the labeled complement for hybridization with the immobilized detection sequence. Thus, if the target sequence is present in the sample, the signal decreases as compared to a sample lacking the target sequence.

The Luminex xMAP technology described above can be used in a competitive binding assay format. In general, this format would comprise a detection molecule immobilized on a labeled bead, a labeled sequence complementary to the detection sequence comprised within the immobilized detection molecule, exposing the immobilized detection sequence and the labeled complement to a nucleic acid sample under hybridizing conditions, and detecting the presence or absence of the target sequence in the sample. The use of the Luminex technology in a competitive binding assay format is described in U.S. Pat. Nos. 5,736,330 and 6,057,107, incorporated herein by reference.

The present invention may be used to protect the identity of the immobilized detection sequence and the labeled complement in a competitive binding assay. For example, to protect the identity of an immobilized detection sequence, one or more masking sequences that mask the identity of the detection sequence also would be immobilized on the support.

Likewise, to protect the identity of the labeled complement, one or more masking sequences that mask the identity of the labeled complement also would be included. In circumstances where the target sequence is amplified prior to hybridization with the detection sequence, it is desirable to associate masking sequence sets with the primer sets used in the amplification, such that attempts to sequence the primer sets is impeded by the presence of the masking sequence sets.

8. Flow Cytometry

Flow cytometry is a useful tool in the analysis of biomolecules. In the context of the present invention, flow cytometry is particularly useful in the analysis of microsphere based assays, such as the Luminex xMAP system. Flow cytometry involves the separation of cells or other particles, such as microshperes, in a liquid sample. Generally, the purpose of flow cytometry is to analyze the separated particles for one or more characteristics. The basic steps of flow cytometry involve the direction of a fluid sample through an apparatus such that a liquid stream passes through a sensing region. The particles should pass one at a time by the sensor and are categorized based on size, refraction, light scattering, opacity, roughness, shape, fluorescence, etc.

In the context of the Luminex xMAP system, flow cytometry can be used for simultaneous sequence identification and hybridization quantification. Internal dyes in the microspheres are detected by flow cytometry and used to identify the specific nucleic acid sequence to which a microsphere is coupled. The label on the target nucleic acid molecule is also detected by flow cytometry and used to quantify target hybridization to the microsphere.

Methods of flow cytometry are well know in the art and are described, for example, in U.S. Pat. Nos. 5,981,180, 4,284,412; 4,989,977; 4,498,766; 5,478,722; 4,857,451; 4,774,189; 4,767,206; 4,714,682; 5,160,974; and 4,661,913, all of which are specifically incorporated by reference.

9. Sequencing

Nucleic acid sequencing techniques can rapidly determine the sequence of a nucleic acid used in an assay. The ability to reverse engineer a nucleic acid assay in this manner makes it easy to copy or circumvent the assay. The present invention is useful for protecting intellectual property in nucleic acid based assays and for impeding the circumvention of nucleic acid based assays because it confounds nucleic acid sequencing analysis. Accordingly, the present invention can be used in any application where one wishes to protect the identity of a specific nucleic acid sequence.

Those skilled in the art are familiar with methods for sequencing DNA. Current DNA sequencing approaches generally incorporate the fundamentals of either the Sanger sequencing method or the Maxam and Gilbert sequencing method, two techniques that were first introduced in the 1970's (Sanger et al., 1977; Maxam and Gilbert, 1977). In the Sanger method, a short oligonucleotide or primer is annealed to a single-stranded template containing the DNA to be sequenced. The primer provides a 3' hydroxyl group, which allows the polymerization of a chain of DNA when a polymerase enzyme and dNTPs are provided. The Sanger method is an enzymatic reaction that utilizes chain-terminating dideoxynucleotides (ddNTPs). ddNTPs are chain-terminating because they lack a 3'-hydroxyl residue, which prevents formation of a phosphodiester bond with a succeeding deoxyribonucleotide (dNTP). A small amount of one ddNTP is included with the four conventional dNTPs in a polymerization reaction. Polymerization or DNA synthesis is catalyzed by a DNA polymerase. There is competition between extension of the chain by incorporation of the conventional dNTPs and termination of the chain by incorporation of a ddNTP.

Both the Sanger and the Maxim-Gilbert methods produce populations of radiolabeled or fluorescently labeled polynucleotides of differing lengths, which are separated according to size by polyacrylamide gel electrophoresis (PAGE). The nucleotide sequence is determined by analyzing the pattern of size-separated labeled polynucleotides in the gel. The Maxim-Gilbert method involves degrading DNA at a specific base using chemical reagents. The DNA strands terminating at a particular base are denatured and electrophoresed to determine the positions of the particular base. By combining the information from fragments terminating at different bases or combinations of bases the entire DNA sequence can be reconstructed. However, the Maxim-Gilbert method involves dangerous chemicals, and is time- and labor-intensive. Thus, it is no longer used for most applications.

The chain-terminator method is readily automated. Three types of automated systems are in use in commercially available DNA sequencers. In the four reaction/four gel system, a primer is linked at its 5' end to a fluorescent dye, and the chain extension reactions are carried out in four separate vessels. The reaction products are then subject to sequencing gel electrophoresis in four parallel lanes and the order in which the fluorescent fragments pass through the gel is recorded by the laser-activated fluorescence detection system. In the four reaction/one gel system, the primers used in each of the four chain extension reactions are each 5' linked to a differently fluorescing dye. The separately reacted mixtures are combined, subjected to sequencing gel electrophoresis in a single lane, and the terminal base on each fragment identified according to its characteristic fluorescence spectrum. In the one reaction/one gel system, each of the four ddNTPs used to terminate chain extension is covalently linked to a differently fluorescing dye, the chain-extension reaction is carried out in a single vessel, the resulting fragment mixture is subjected to sequencing gel electrophoresis in a single lane, and the terminal base on each fragment is identified according to its characteristic fluorescence spectrum.

Regardless of the sequencing method used, the masking nucleic acid sequences of the present invention can be used to impede sequence analysis of the detection nucleic acid sequence. For example, if a detection nucleic acid sequence is masked by three masking nucleic acid sequences, the sequence analysis would be nonsensical indicating an A, T, G, and C at every nucleic acid position in the sequence.

C. Kits

Any of the compositions described herein may be comprised in a kit. In a non-limiting example, a detection nucleic acid molecule and a masking nucleic acid molecule may be comprised in a kit in suitable container means. In certain embodiments, the detection nucleic acid molecule and a plurality of masking nucleic acid molecules may be comprised in a kit. It may also include one or more buffers, such as hybridization buffer or a wash buffer. Other kits of the invention may include components for making a nucleic acid array, and thus, may include, for example, a solid support. In some aspects of the invention, the kits will comprise pre-fabricated arrays, such as, for example, microspheres coupled with a detection nucleic acid molecule and one or more masking nucleic acid molecules.

The kits may comprise suitably aliquoted nucleic acid compositions of the present invention, whether labeled or unlabeled, as may be used to isolate, separate, detect, or amplify a targeted nucleic acid. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional containers into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one or more liquid solutions, the liquid solution may be an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

A kit will also include instructions for employing the kit components as well the use of any other reagent not included in the kit. Instructions may include variations that can be implemented.

D. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Sequence-Specific Oligonucleotide Hybridization in the Presence of Masking Sequences Using the Luminex xMAP Multiplexing System The inventors used the Luminex xMAP multiplexing system to demonstrate the feasibility of using masking sequences in sequence-specific oligonucleotide hybridization assays. The xMAP system utilizes fluorescently coded microspheres as an assay reaction surface to capture and detect the presence of various biomolecules. A potential caveat of using masking oligonucleotides in the xMAP system is the potential to reduce sensitivity due to a reduction in the total number of specific probes coupled to each microsphere. However, the inventors demonstrated that the sensitivity of the system to binding sample DNA is either not reduced or only slightly reduced in the presence of one, two, or three masking nucleic acid molecules co-conjugated with a specific detection nucleic acid molecule to the surface of the microsphere.

Coupling Oligonucleotides to the Luminex Microshperes. Detection Nucleic Acid Molecules and Masking Nucleic Acid Molecules were synthesized with a 5' amine, 12 carbon linker. The sequences of the oligonucleotides were as follows: Detection Molecule, 5'-TCA GAC AAT TTA GAT TTG-3' (SEQ ID NO: 9); Masking Molecule, 5'-AAG CGA TGC ACG CGC ACT-3'1 (SEQ ID NO: 10); Masking Molecule, 5'-CGC TTT GTG CAC TTG CAA-3'2 (SEQ ID NO: 11); and Masking Molecule, 5'-GTT ACG CCA GGT ACA GGC-3'3 (SEQ ID NO: 12).

Luminex xMAP carboxylate microspheres ($1.25\times10^7$) were dispensed into a 1.5 mL microcentrifuge tube, pelleted and resuspended with 50 μL of 0.1 M MES, pH 4.5. A total of 1 nmole of oligonucleotide was added to the microspheres in the following four combinations: (1) 1 nmole Detection Molecule; (2) 0.5 nmoles Detection Molecule+0.5 nmoles Masking Molecule 1; (3) 0.33 nmoles Detection Molecule+0.33 nmoles Masking Molecule 1+0.33 nmoles Masking Molecule 2; (4) 0.25 nmoles Detection Molecule+0.25 nmoles Masking Molecule 1+0.25 nmoles Masking Molecule 2+0.25 nmoles Masking Molecule 3. The oligonucleotides and beads were vortexed briefly.

Immediately before use, a 10 mg/mL solution of EDC in 0.1 M MES (2-(N-morpholino)ethanesulfonic acid; pH 4.5) was prepared and 2.5 μL was added to the bead/oligonucleotide mixture. The mixture was incubated for 30 minutes at room temperature in the dark. A second aliquot of EDC solution was prepared, added to the microsphere mixture, and incubated for an additional 30 minutes. Following the two incubation steps, the coupled microspheres were washed first with 1.0 mL of Tween® 20 (0.02% v/v) followed by 1.0 mL of SDS (sodium dodecyl sulfate; 0.1% w/v). The coupled microspheres were resuspended in 1.25 mL of TE (10 mM Tris-HCl, 1 mM EDTA; pH 8.0) and stored at 2-8° C. protected from light.

DNA Hybridization and Detection. A 5' biotinylated oligonucleotide, complementary to the Detection Sequence, was used to determine the efficiency of coupling and the effect of the Masking Sequences on hybridization efficiency and sensitivity.

The Detection Sequence complement was diluted to 1000, 316, 100, 31.6, 10, 3.16 and 1 amol/μL in TE and 10 μL of diluted complement was added individually to wells of a 96 well Costar® Thermowell™ plate. TE alone (10 μL) was added to empty wells to represent the background. An additional 15 μL of TE was added to each well.

Coupled microspheres were diluted individually in 1.5× hybridization solution (4.5 M tetramethylammonium chloride, 75 mM Tris-HCl, 6 mM EDTA, pH 8.0, 0.15% Sarkosyl) to a concentration of 100 beads/μL. Diluted microspheres (50 μL; 5000 microspheres total) representing either Detection Molecule-coupled microspheres, Detection Molecule+Masking Molecule 1-coupled microspheres, Detection Molecule+Masking Molecules 1 & 2-coupled microspheres, or Detection Molecule+Masking Molecules 1 & 2 & 3-coupled microspheres were added to individual wells in duplicate, and the plate was incubated at 95° C. for 5 minutes. The plate was transferred to a heat block warmed to 45° C. and was incubated for 45 minutes in the dark.

The samples were centrifuged at 2250×g for 2 minutes, and the supernatant was removed. Streptavidin-R-phycoerythrin (20 μg/ml; 50 μL) diluted in 1× hybridization buffer was added to each well, and the samples were incubated 15 minutes at room temperature in the dark. The samples were analyzed on a Luminex 100 instrument.

Figure 2A:
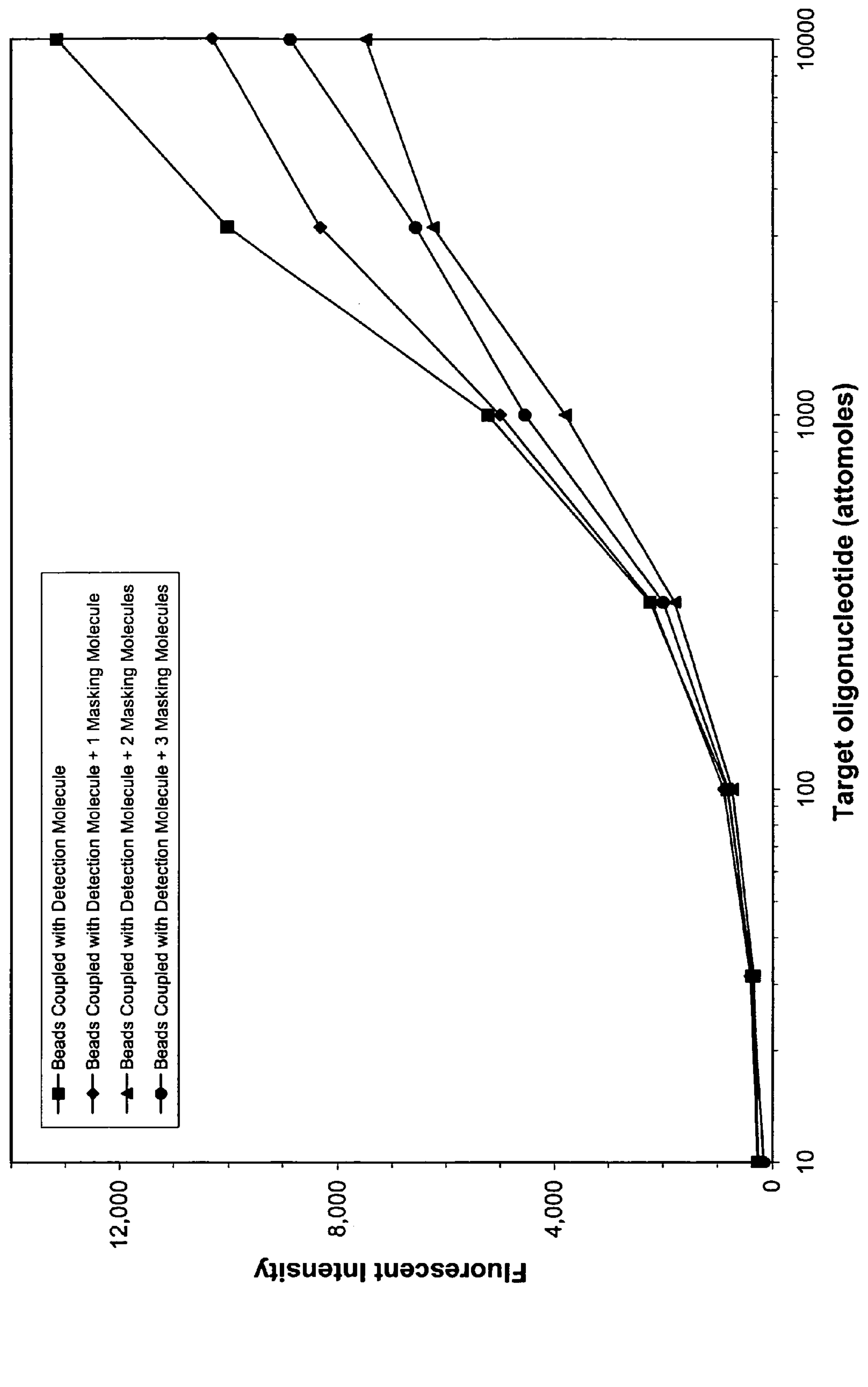

As shown in FIG. 2A and FIG. 2B, the Luminex system was able to capture and detect the target oligonucleotide on microspheres coupled with Detection Molecule alone or coupled with Detection Molecule plus one, two, or three Masking Molecule.

Figure 3A:
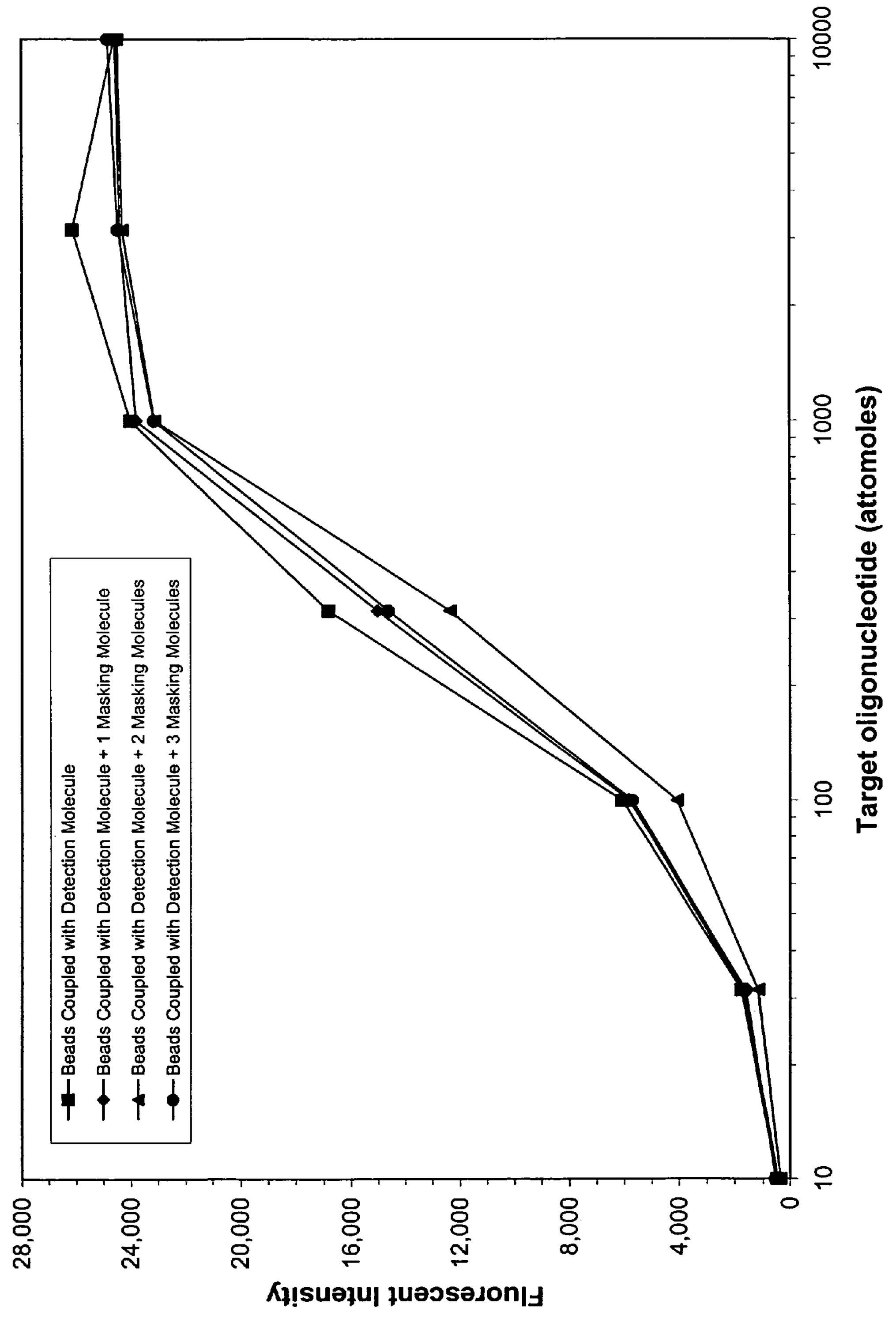

FIG. 3A and FIG. 3B show a similar assay, but using a signal amplification process. The signal amplification process is the same as above for all procedural steps up to and including the 45 minute incubation. However, following the 45 minute incubation, samples were washed by centrifugation at 2250×g for 2 minutes followed by removal of the supernatant. The samples then were washed two additional times with 100 μL of 0.5× hybridization buffer. Streptavidin-R-phycoerythrin (20 μg/ml; 50 μL) diluted in PBS-BSA (phosphate-buffered saline, 1% w/v bovine serum albumin; pH 7.4) was added to each well, and the samples were incubated 15 minutes at room temperature in the dark.

The samples were washed once with 100 μL of PBS-BSA, and 50 μL of anti-streptavidin and normal goat IgG (5 μg/mL and 100 μg/mL, respectively) diluted with PBS-BSA was added to each well. The samples were incubated for an additional 60 minutes at room temperature in the dark. The samples were washed once with 100 μL of PBS-BSA, and 50 μL of streptavidin-R-phycoerythrin (20 μg/ml) diluted in PBS-BSA was added to each well. The samples were incubated 15 minutes at room temperature in the dark. The samples were washed one final time with PBS-BSA and resuspended with 65 μL of PBS-BSA. The samples were analyzed on a Luminex 100 instrument.

Example 2

Detection of PCR™ Amplicons From Human Patient Samples by Sequence-Specific Oligonucleotide Hybridization in the Presence of Masking Sequences Using the Luminex xMAP Multiplexing System To further demonstrate the feasibility of using masking sequences in sequence-specific oligonucleotide hybridization assays the inventors used the Luminex xMAP multiplexing system to detect alleles amplified from three different patient samples.

Patient Samples. Purified Reference DNA samples were ordered from UCLA Immunogenetics Center. The samples were of previously identified DQ-alpha HLA types. Two samples were known to be representative of the Detection Sequence. An additional sample was known to be negative for the Detection Sequence.

PCR Amplification. Primer Sequence Sets were purchased commercially. The forward Primer Sequence is 5'-ATG GTG TAA ATC TGT ACC AGT-3' (SEQ ID NO: 13), and the reverse Primer Sequence is 5'-TTG GTA GCA GCG GTA GAG TTG-3' (SEQ ID NO: 14). Both of the above mentioned primers were ordered with 5' biotin modifications.

Primers were diluted to a final concentration of 0.4 μM in $dH_20$. Amplification mixture was created by adding 125 μL of HotStarTaq Master Mix (Qiagen mat# 1010023), 110 μL of $diH_20$, and 10 μL of primers and 49 μL was aliquoted into 4 separate 0.2 mL PCR™ tubes and capped. The three purified DNA samples (1 μL) were added to individual tubes. No template was added to the fourth tube to represent a PCR™ background.

The PCR™ amplification protocol was as follows: (1) An initial activation step at 95° C. for 15 minutes. (2) A 3-step cycle of 94° C. for 30 seconds (denaturing), 63° C. for 30 seconds (annealing), and 72° C. for 30 seconds (extension). (3) Run this cycle 35 times. (4) Finally, a 72° C. final extension for 3 minutes. Samples were removed from the thermalcycler and stored at 4° C.

Coupling Oligonucleotides to the Luminex Microshperes. The detection nucleic acid molecules and masking nucleic acid molecules were coupled to the Luminex microspheres as described in Example 1.

DNA Hybridization. The amplified DNA patient samples were hybridized to nucleic acid molecule-coupled microspheres essentially as described in Example 1. Amplified samples (10 μL) were added to microtiter wells with an additional 15 μL of TE. TE (25 μL) was added to an additional well to represent the background. The signal amplification process was not used during this procedure.

Figure 4A:
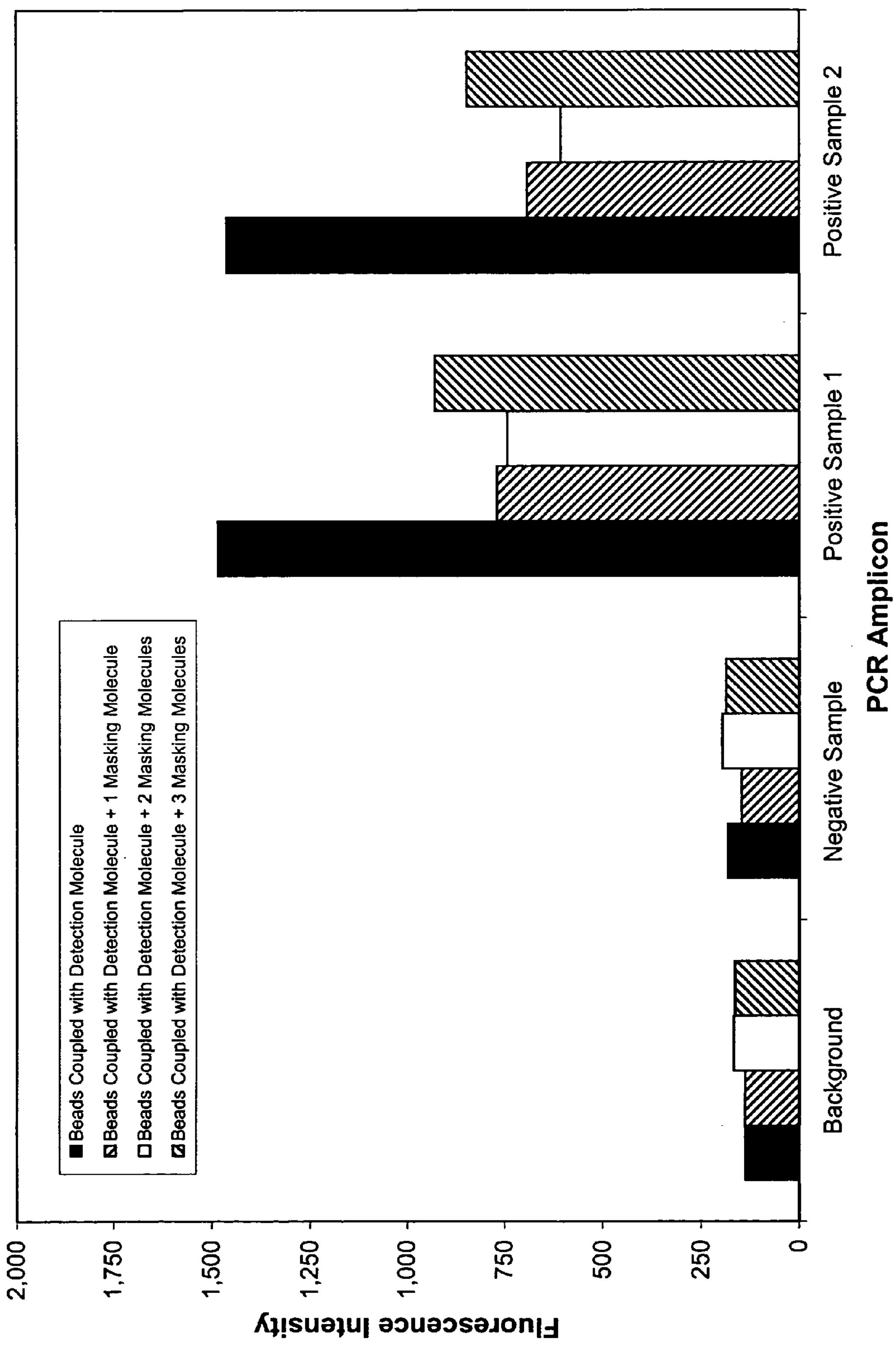

As shown in FIG. 4A and FIG. 4B, the Luminex xMAP system was able to capture and detect the PCR™ amplicons on beads coupled with a detection nucleic acid molecule alone or coupled with a detection nucleic acid molecule plus one, two, or three masking nucleic acid molecules. The sensitivity of the system to detect amplified patient sample DNA is only slightly reduced in the presence of one, two, or three masking nucleic acid molecules co-conjugated with Detection Nucleic Acid Molecules to the surface of the microsphere.

Example 3

PCR Amplification of Human Patient Samples with Primer Sequence Sets Alone or in the Presence of Masking Sequence Primer Sets To further demonstrate the feasibility of masking sequences, the inventors amplified human patient samples using PCR™ amplification with specific primer sets alone or in the presence of one, two, or three masking sequence primer sets. The amplified samples were then detected using detection nucleic acid molecule-coupled xMAP microspheres. The same human patient DNA samples were used for this example as were used in Example 2.

PCR Amplification. Masking Sequence Primer Sets were ordered commercially. The forward and reverse specific primers were identical to those listed in Example 2 (forward specific primer, 5'-ATG GTG TAA ATC TGT ACC AGT-3' (SEQ ID NO:13); reverse specific primer, 5'-TTG GTA GCA GCG GTA GAG TTG-3' (SEQ ID NO:14)). The forward Masking Sequence Primer 1 is 5'-TCT CCT AGG TAC ATC TAA TCC-3' (SEQ ID NO: 15), and the reverse Masking Sequence Primer 1 is 5'-ACT CCG CAG CAT CCG CGT ACT-3' (SEQ ID NO: 16), and the forward Masking Sequence Primer 2 is 5'-GAA TAA CTC GGG CCG GGT GCG-3' (SEQ ID NO: 17), and the reverse Masking Sequence Primer 2 is 5'-CAA TAC TGC TGA TAC TTA CAA-3' (SEQ ID NO: 18), and the forward Masking Sequence Primer 3 is 5'-CGC AGC GCT CTA GAA CTG CAA-3' (SEQ ID NO: 19), and the reverse Masking Sequence Primer 3 is 5'-GGC AGT ATT ATC AGT ACC GGC-3' (SEQ ID NO: 20). All of the above mentioned primers were ordered with 5' biotin modifications.

The PCR™ amplification was performed as described in Example 2 except that primer masking sequence sets were added to the specific primer dilutions as described below. Primers were added to separate tubes in the following four combinations: (1) 0.4 μM of the Specific Primer Set; (2) 0.2 μM of the Specific Primer Set+0.2 μM of Masking Primer Set 1; (3) 0.13 μM of the Specific Primer Set+0.13 μM of Masking Primer Set 1; +0.13 μM of Masking Primer Set 2; (4) 0.1 μM of the Specific Primer Set+0.1 μM of Masking Primer Set 1; +0.1 μM of Masking Primer Set 2+0.1 μM of Masking Primer Set 3.

Coupling Oligonucleotides to the Luminex Microspheres. The Detection Nucleic Acid Molecule was coupled to the Luminex microspheres as described in Coupling 1 from Example 1.

Figure 5A:
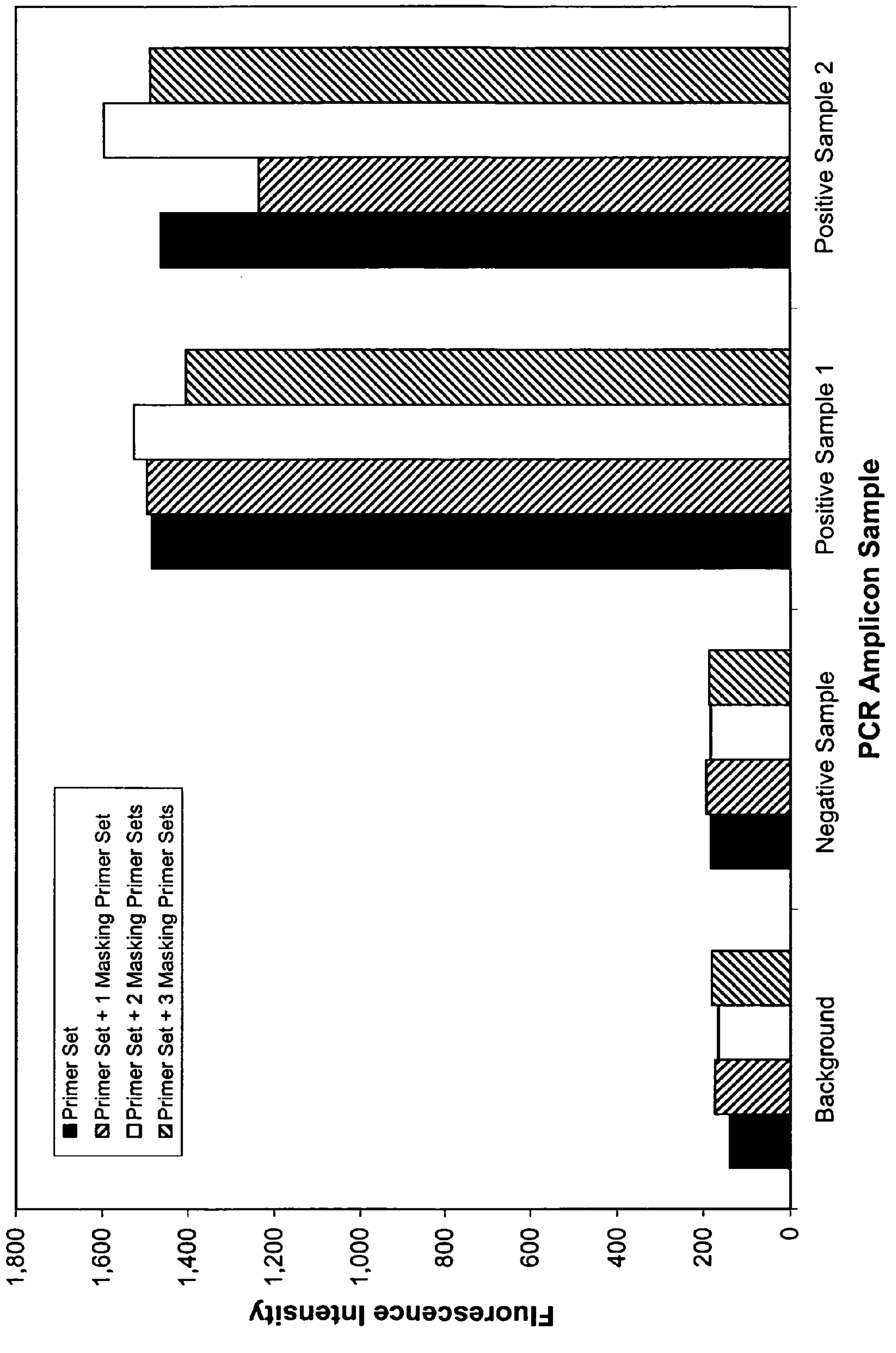

DNA Hybridization and Detection. The DNA hybridization was performed as described in Example 1. As shown in FIG. 5A and FIG. 5B, the Luminex xMAP system was able to capture and detect the PCR™ amplicons amplified with a specific primer set alone or amplified with a specific primer set plus one, two, or three Masking Sequence Primer Sets. The results demonstrate that there was no reduction in hybridization signal generated from amplicons produced with only a specific primer set alone or amplicons produced with a specific primer set plus one, two, or three Masking Sequence Primer Sets.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,284,412
U.S. Pat. No. 4,498,766
U.S. Pat. No. 4,659,774
U.S. Pat. No. 4,661,913
U.S. Pat. No. 4,682,195
U.S. Pat. No. 4,683,202
U.S. Pat. No. 4,714,682
U.S. Pat. No. 4,767,206
U.S. Pat. No. 4,774,189
U.S. Pat. No. 4,816,571
U.S. Pat. No. 4,857,451
U.S. Pat. No. 4,959,463
U.S. Pat. No. 4,989,977
U.S. Pat. No. 5,141,813
U.S. Pat. No. 5,160,974
U.S. Pat. No. 5,264,566
U.S. Pat. No. 5,279,721
U.S. Pat. No. 5,428,148
U.S. Pat. No. 5,478,722
U.S. Pat. No. 5,539,082
U.S. Pat. No. 5,554,744
U.S. Pat. No. 5,574,146
U.S. Pat. No. 5,602,244
U.S. Pat. No. 5,645,897
U.S. Pat. No. 5,705,629
U.S. Pat. No. 5,714,331
U.S. Pat. No. 5,719,262
U.S. Pat. No. 5,736,330
U.S. Pat. No. 5,736,336
U.S. Pat. No. 5,766,855
U.S. Pat. No. 5,773,571
U.S. Pat. No. 5,786,461
U.S. Pat. No. 5,837,832
U.S. Pat. No. 5,837,860
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,891,625
U.S. Pat. No. 5,900,481
U.S. Pat. No. 5,905,024
U.S. Pat. No. 5,908,845
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 5,981,180
U.S. Pat. No. 5,981,180
U.S. Pat. No. 6,057,107
Egholm et al., *Nature,* 365(6446):566-568, 1993.
EP 266,032
European Appln. 320 308
European Appln. 329 822
Fodor et al., *Biochemistry,* 30(33):8102-8108, 1991.
Froehler et al., *Nucleic Acids Res.,* 14(13):5399-5407, 1986.
Frohman, In: PCR™ *Protocols: A Guide To Methods And Applications*, Academic Press, N.Y., 1990.
GB Appln. 2 202 328
Holmstrom et al., *Anal. Biochem.* 209:278-283, 1993.
Koshkin and Dunford, *J. Biol. Chem.,* 273(11):6046-6049, 1998.
Koshkin and Wengel, *J. Org. Chem.,* 63(8):2778-2781, 1998.

Kwoh et al., *Proc. Natl. Acad. Sci. USA,* 86:1173, 1989.

Maxam, et al., *Proc. Natl. Acad. Sci. USA,* 74:560, 1977.

Newton et al., *Nucl. Acids Res.* 21:1155-1162, 1993.

Ohara et al., *Proc. Natl. Acad. Sci. USA,* 86:5673-5677, 1989.

PCT Appln. PCT/US87/00880

PCT Appln. PCT/US89/01025

PCT WO 88/10315

PCT WO 89/06700

PCT WO 90/07641

PCT WO 92/20702

PCT/EP/01219

Pease et al., *Proc. Natl. Acad. Sci. USA,* 91:5022-5026, 1994.

Rasmussen et al., *Anal. Biochem,* 198:138-142, 1991.

Running et al., *BioTechniques* 8:276-277, 1990.

Sambrook et al., *In: Molecular cloning*, Cold Spring Harbor Laboratory Press, Cold Spring Harbor, N.Y., 2001.

Sanger et al., *Proc. Natl. Acad. Sci. USA,* 74:5463-5467, 1977.

Wahlestedt et al., *Proc. Natl. Acad. Sci. USA,* 97(10):5633-5638, 2000.

Walker et al., *Nucleic Acids Res.,* 20(7):1691-1696, 1992.

---

What is claimed is:

1. A method of masking the identity of a detection sequence on a nucleic acid molecule comprising:

(a) obtaining a detection nucleic acid molecule comprising a known detection sequence that hybridizes to a target nucleic acid sequence of interest in a sample during a hybridization assay;

(b) designing and making a first masking nucleic acid molecule comprising a first masking sequence, wherein the first masking nucleic acid molecule is the same length as the detection nucleic acid molecule and does not hybridize to a nucleic acid sequence in the sample during the hybridization assay, and wherein the masking sequence varies from the detection sequence at at least half of its nucleic acid positions, (c) masking the identity of the detection sequence on the detection nucleic acid molecule by combining the detection nucleic acid molecule and the first masking nucleic acid molecule on the same solid support or in the same solution if the detection nucleic acid molecule and the first masking nucleic acid molecule are not immobilized on solid supports, whereby upon nucleic acid sequence analysis the presence of both the detection nucleic acid molecule and the first masking nucleic acid molecule produce a nonsensical nucleotide sequence at at least half of the nucleic acid positions in the detection sequence.

2. The method of claim 1, wherein the masking sequence of the first masking nucleic acid molecule varies from the detection sequence at all positions.

3. The method of claim 1, further comprising combining with said detection nucleic acid molecule and said first masking nucleic acid molecule a second masking nucleic acid molecule on the same solid support or in the same solution, wherein the second masking nucleic acid molecule is the same length as the detection nucleic acid molecule and does not hybridize to a nucleic acid sequence in the sample during the hybridization assay, and wherein the second masking nucleic acid molecule comprises a second masking sequence that varies from the detection sequence and the first masking sequence at at least half of its nucleic acid positions.

4. The method of claim 3, wherein the second masking sequence varies from the detection sequence and the first masking sequence at all positions.

5. The method of claim 3, further comprising combining with said detection nucleic acid molecule and said first and second masking nucleic acid molecules a third masking nucleic acid molecule on the same solid support or in the same solution, wherein the third masking nucleic acid molecule is the same length as the detection nucleic acid molecule and does not hybridize to a nucleic acid sequence in the sample during the hybridization assay, and wherein the third masking nucleic acid molecule comprises a third masking sequence that varies from the detection sequence and the first and second masking sequences at at least half of its nucleic acid positions.

6. The method of claim 5, wherein the third masking sequence varies from the detection sequence and the first and second masking sequences at all positions.

7. The method of claim 1, wherein the detection sequence is comprised within a hybridization probe.

8. The method of claim 7, wherein the hybridization probe is labeled.

9. The method of claim 8, wherein the label is biotin.

10. The method of claim 1, wherein the detection nucleic acid molecule is a primer.

11. The method of claim 10, wherein the primer is labeled.

12. The method of claim 11, wherein the label is biotin.

13. The method of claim 11, wherein the label is a fluorescent molecule.

14. The method of claim 13, wherein the primer further comprises a fluorescence quencher.

15. The method of claim 1, wherein the nucleotide sequence of the masking sequence is determined using an algorithm.

16. The method of claim 15, wherein for each nucleotide position of the detection sequence a complementary nucleotide is positioned in the masking sequence using the algorithm: Masking Sequence 1 contains complementary nucleotides at nucleotide position 1 and every third nucleotide thereafter, Masking Sequence 2 contains complementary nucleotides at nucleotide position 2 and every third nucleotide thereafter, and Masking Sequence 3 contains complementary nucleotides at nucleotide position 3 and every third nucleotide thereafter.

17. The method of claim 1, wherein the detection nucleic acid molecule and the masking molecule(s) are combined on a solid support.

18. The method of claim 17, wherein the solid support is a bead.

19. The method of claim 17, wherein the solid support is a column.

20. The method of claim 1, wherein the detection nucleic acid molecule and the masking nucleic acid molecule further comprise an equilibrium sequence.

21. The method of claim 1, wherein the detection sequence and the masking sequence are from 10 to 60 nucleotides in length.

22. The method of claim 1, wherein the detection nucleic acid molecule and the masking molecule(s) are combined in a solution.

23. The method of claim 1, further comprising detecting the selective hybridization of the detection sequence to the target nucleic acid sequence.

24. A method of performing a hybridization reaction comprising the steps of:

(a) providing a hybridization probe, which comprises a hybridization sequence designed to hybridize to a target sequence in a sample during a hybridization reaction;

(b) providing a first masking nucleic acid molecule that comprises a first masking sequence, wherein the first masking nucleic acid molecule is the same length as the hybridization probe and does not hybridize to a nucleic acid sequence in the sample during the hybridization reaction, and wherein the masking sequence of the first masking nucleic acid molecule varies from the hybridization sequence at at least half of its nucleic acid positions, and further wherein the first masking nucleic acid molecule has a reduced ability or inability to hybridize to the target;

(c) masking the identity of the hybridization sequence on the nucleic acid molecule by combining the hybridization probe and the first masking nucleic acid molecule on the same solid support or in the same solution if the hybridization probe and the first masking nucleic acid molecule are not immobilized on solid supports, whereby upon nucleic acid sequence analysis the presence of both the hybridization probe and the first masking nucleic acid molecule produce a nonsensical nucleotide sequence at at least half of the nucleic acid positions in the hybridization sequence;

(d) performing the hybridization reaction comprising the hybridization probe and the first masking nucleic acid molecule in the presence of the target sequence under conditions permitting the selective hybridization of the hybridization probe to the target sequence.

25. The method of claim 24, wherein the masking sequence of the first masking nucleic acid molecule varies from the hybridization sequence at all positions.

26. The method of claim 24, comprising providing a second masking nucleic acid molecule comprising a second masking sequence that varies from the hybridization sequence and the first masking sequence at at least half of its nucleic acid positions, wherein the second masking nucleic acid molecule is the same length as the hybridization probe and does not significantly hybridize to a nucleic acid sequence in the sample during the hybridization reaction, and wherein the second masking nucleic acid molecule has a reduced ability or inability to hybridize to the target; and combining the second masking nucleic acid molecule with the hybridization probe and the first masking nucleic acid molecule on the same solid support or in the same solution.

27. The method of claim 26, wherein the second masking sequence varies from the hybridization sequence and the first masking sequence at all positions.

28. The method of claim 26, comprising providing a third masking nucleic acid molecule comprising a third masking sequence that varies from the hybridization sequence and the first and second masking sequences at at least half of its nucleic acid positions, wherein the third masking nucleic acid molecule is the same length as the hybridization probe and does not significantly hybridize to a nucleic acid sequence in the sample during the hybridization reaction, and wherein the third masking nucleic acid molecule has a reduced ability or inability to hybridize to the target; and combining the third masking nucleic acid molecule with the hybridization probe, the first masking nucleic acid molecule, and the second masking nucleic acid molecule on the same solid support or in the same solution.

29. The method of claim 28, wherein the third masking sequence varies from the hybridization sequence and the first and second masking sequences at all positions.

30. The method of claim 24, wherein the hybridization sequence and the masking sequence are from 10 to 60 nucleotides in length.

31. The method of claim 24, wherein the hybridization probe and the masking nucleic acid molecule further comprise an equilibrium sequence.

32. The method of claim 24, wherein the hybridization probe and the masking molecule(s) are combined in a solution.

33. The method of claim 24, wherein the hybridization probe and the masking molecule(s) are combined on a solid support.

34. The method of claim 24, further comprising detecting the selective hybridization of the hybridization probe to the target sequence.

* * * * *